US007642080B2

(12) United States Patent
Nielsen et al.

(10) Patent No.: US 7,642,080 B2
(45) Date of Patent: Jan. 5, 2010

(54) SUBTILASES

(75) Inventors: Preben Nielsen, Horsholm (DK); Martin Borchert, Copenhagen O (DK)

(73) Assignee: Novozymes A/S, Bagsvaerd (DK)

( * ) Notice: Subject to any disclaimer, the term of this patent is extended or adjusted under 35 U.S.C. 154(b) by 455 days.

(21) Appl. No.: 11/504,743

(22) Filed: Aug. 15, 2006

(65) Prior Publication Data

US 2007/0196898 A1 Aug. 23, 2007

Related U.S. Application Data

(60) Provisional application No. 60/722,517, filed on Sep. 30, 2005, provisional application No. 60/709,403, filed on Aug. 18, 2005.

(30) Foreign Application Priority Data

Aug. 16, 2005 (DK) .............................. 2005 01155
Sep. 30, 2005 (DK) .............................. 2005 01366

(51) Int. Cl.
*C12N 9/54* (2006.01)
*C12N 15/57* (2006.01)
*C12N 15/74* (2006.01)
*C12N 15/75* (2006.01)
*C11D 3/386* (2006.01)

(52) U.S. Cl. .................. 435/221; 435/69.1; 435/252.3; 435/252.31; 435/320.1; 510/300; 510/392

(58) Field of Classification Search ....................... None
See application file for complete search history.

(56) References Cited

U.S. PATENT DOCUMENTS 6,541,235 B1 * 4/2003 Bryan ........................ 435/221
7,262,042 B2 * 8/2007 Weber et al. ................ 435/212

FOREIGN PATENT DOCUMENTS

WO WO 03/054185 7/2003

* cited by examiner

*Primary Examiner*—Anand U Desai
*Assistant Examiner*—William W Moore
(74) *Attorney, Agent, or Firm*—Elias Lambiris

(57) ABSTRACT

The present invention relates to novel subtilases from wild-type strains of *Bacillus*, especially the *Bacillus* strains ZI344, EP655, P203, EP63, ZI120, ZI130, ZI1342 and ZI140, and to methods of construction and production of these proteases. Further, the present invention relates to use of the claimed subtilases in detergents, such as a laundry detergent or an automatic dishwashing detergent.

7 Claims, 6 Drawing Sheets

```
  1 -------CAGATGAAGTTGAGCAGGTTGGCGTATTCTCTATTGAAGAAGATCAGCAAAAAGAAGATTCGA EP655
  1 ---------------------CAGGTTGGCGTATTCTCTATTGAAGAAGATCAGCAAAAAGAAGATTCGA p203
  1 ------ACAGATGAAGTTGAGCAGGTTGGCGTATTCTCTATTGAAGAAGATCAGCAAAAAGAAGATTCGA ZI120
  1 ---------GATGAAGTTGAGCAGGTTGGCGTATTCTCTATTGAAGAAGATCAGCAAAAAGAAGATTCGA EP63
  1 ---TTTACAGATGAAGTTGAGCAGGTTGGCGTATTCTCTATTGAAGAAGATCAGCAAAAAGAAGATTCGA ZI130
  1 ------ACAGATGAAGTTGAACAGGTTGGCGTATTCTCTATTGAAGAAGATCAGCAAAAAGAAGATTCGA ZI132
  1 A-------------------------------------------------CTCAGCATGATGATGA---GG ZI340
  1 AGCCTTGCAAACGAGGTTGAACAGGTAGGCGTTTTCACTACAGATGAAACTCAGCATGATGATGA---GA ZI344
  1 ---C--ACTGAGGAAATTGACCAAGTTGGTGTATTTTCTGTTGAAGAACAAAGTGTAGCTGAGGATACGT PD138
 64 CTGATATTGATGTAGACATTATTTTTGATTACGATTATATTCCCGTATTATCAGTTGAGTTGGACCCTGA EP655
 50 CTGATATTGATGTAGACATTATTTTTGATTACGATTATATTCCCGTATTATCAGTTGAGTTGGACCCTGA p203
 65 CTGATATTGATGTAGACATTATTTTTGATTACGATTATATTCCCGTATTATCAGTTGAGTTGGACCCTGA ZI120
 62 CTGATATTGATGTAGACATTATTTTTGATTACGATTATATTCCCGTATTATCAGTTGAATTGGATCCTGA EP63
 68 CTGATATTGATGTAGACATTATTTTTGATTACGATTATATTCCCGTATTATCAGTTGAGTTGGACCCTGA ZI130
 65 CTGATATTGATGTAGACATTATTTTTGATTACGATTATATTCCCGTATTATCAGTTGAATTGGATCCTGA ZI132
 20 C---TATTGATGTTGATATTATTTATGATTATGATTATATCCCAGTCTTATCAGTAGAGATCGATCCTGA ZI340
 68 C---GATTGATGTTGATATTATTTATGATTATGATTATATTCCAGTCTTATCAGTAGAGATTGATCCTGA ZI344
 66 TAGATATTGATGTAGACATTATTGATGAATATGATTATATTGATGTGTTAGCTGTAGAATTAGATCCTGA PD138
134 AGATGTTGATGCATTAAGTGAAGAAGATGGAATCGCATATATTGAAGAAGACTTTGAAGTATCAATCCAG EP655
120 AGATGTTGATGCATTAAGTGAAGAAGATGGAATCGCATATATTGAAGAAGACTTTGAGGTATCAATCCAG p203
135 AGATGTTGATGCATTAAGTGAAGAAGATGGAATCGCATATATTGAAGAAGACTTTGAAGTATCAATCCAG ZI120
132 AGATGTTGATGCATTAAGTGAAGAAGATGGAATCGCATATATTGAAGAAGACTTTGAGGTATCAATTCAG EP63
138 AGATGTTGATGCATTAAGTGAAGAAGATGGAATCGCATATATTGAAGAAGACTTTGAGGTATCAATCCAG ZI130
135 AGATGTTGATGCATTAAGTGAAGAAGATGGAATCGCATATATTGAAGAAGACTTTGAGGTATCAATTCAG ZI132
 87 AGATGTCGAGGTACTCAGTCAAGAAGAAGGCATTGCCTATATTGAGGAAGACTTTGAAGTATCCATTCAA ZI340
135 GGATGTAGAAGCACTTAGTCAAGAAGAAGGCATTGCCTATATTGAGGAAGACTTTGAAGTATCTATTCAA ZI344
136 GGATGTAGATGCGTTAAGTGAAGAAGCAGGTATCTCATTTATTGAAGAAGACATTGAACTGTCTATTCAA PD138
204 CAATCGGTGCCTTGGGGTATTACTCGTGTACAAGCTCCAGCAGCGATTAACCGTGGAACAAATGGTTCAG EP655
```

Fig. 2

190 CAATCGGTGCCTTGGGGTATTACTCGTGTACAAGCTCCAGCAGCGATTAACCGTGGAACAAATGGTTCAG p203

205 CAATCGGTGCCTTGGGGTATTACTCGTGTACAAGCTCCAGCAGCGATTAACCGTGGAACAAATGGTTCAG ZI120

202 CAATCGGTGCCTTGGGGTATTACTCGTGTACAAGCTCCAGCAGCGATTAACCGTGGAACAAATGGTTCAG EP63

208 CAATCGGTGCCTTGGGGTATTACTCGTGTACAAGCTCCAGCAGCGATTAACCGTGGAACAAATGGTTCAG ZI130

205 CAATCGGTGCCTTGGGGTATTAATCGTGTACAAGCTCCAACAGCGATTAACCGTGGAACAAATGGTTCAG ZI132

157 CAGACTGTACCTTGGGGCATTCAAAGAGTACAAGCTCCTGCAGTTATTAATCGTGGCATTAATGGCAGTG ZI340

205 CAGACTGTTCCTTGGGGCATTCAAAGAGTACAAGCTCCTGCAGTTATTAATCGTGGCATTAATGGTAGCG ZI344

206 CAAACAGTTCCTTGGGGCATTACTCGTGTACAAGCTCCGGCTGTTCATAACCGTGGGATTACAGGTTCTG PD138

274 GAGTAAGAGTGGCTGTATTGGATACAGGAATTTCTACACATAGTGATTTAACAATTCGTGGTGGAGCTAG EP655

260 GAGTAAGAGTGGCTGTATTGGATACAGGAATTTCTACACATAGTGATTTAACAATTCGTGGTGGAGCTAG p203

275 GAGTAAGAGTGGCTGTATTGGATACAGGAATTTCTACACATAGTGATTTAACAATTCGTGGTGGAGCTAG ZI120

272 GAGTAAGAGTGGCTGTATTGGATACAGGAATTTCTACACATAGTGATTTAACAATTCGTGGTGGAGCTAG EP63

278 GAGTAAGAGTGGCTGTATTGGATACAGGAATTTCTACACATAGTGATTTAACAATTCGTGGTGGAGCTAG ZI130

275 GAGTAAGAGTGGCTGTATTGGATACAGGAATTTCTACACATAGTGATTTAACAATTCGTGGTGGAGCTAG ZI132

227 GGGTACGAGTAGCGGTGCTTGATTCAGGCATTTCCACTCATAGTGATTTAAGCATTTCCGGTGGCGTAAG ZI340

275 GGGTGCGAGTAGCGGTGCTTGATTCAGGCATTTCCTCCCATAGTGATTTAAGCATTTCTGGTGGTGTAAG ZI344

276 GAGTAAGAGTAGCTATCCTTGATTCAGGGATTTCAGCCCATAGTGATTTGAATATCCGCGGTGGAGCTAG PD138

344 CTTCGTGCCTGGTGAACCAAATACATCTGACTTAAATGGCCATGGTACCCATGTAGCTGGAACAATTGCA EP655

330 CTTCGTGCCTGGTGAACCAAATACATCTGACTTAAATGGCCATGGTACCCATGTAGCTGGAACAATTGCA p203

345 CTTCGTGCCTGGTGAACCAAATACATCTGACTTAAATGGCCATGGTACCCATGTAGCTGGAACAATTGCA ZI120

342 CTTCGTGCCTGGTGAACCAAATACATCTGACTTAAATGGCCATGGTACCCATGTAGCGGGAACAATTGCA EP63

348 CTTCGTGCCTGGTGAACCAAATACATCTGACTTAAATGGCCATGGTACCCATGTAGCTGGAACAATTGCA ZI130

345 CTTCGTGCCTGGTGAACCAAATACATCTGACTTAAATGGCCATGGTACTCATGTAGCGGGAACAATTGCA ZI132

297 CTTTGTCCCTGGTGAACCAACTATTTCTGATGGAAATGGCCATGGTACACATGTAGCGGGAACGATTGCT ZI340

345 CTTTGTTCCTGGTGAACCAACCATAGCCGATGGAAATGGGCACGGGACACACGTAGCTGGAACGATTGCT ZI344

346 CTTTGTACCGGGTGAACCAACGACAGCTGATTTAAATGGACATGGTACTCACGTGGCCGGAACAGTAGCA PD138

414 GCTTTGAATAACTCAATCGGCGTTGTAGGTGTAGCACCAAATGCTGATCTWTATGCTGTAAAAGTTCTTG EP655

400 GCTTTGAATAACTCAATCGGCGTTGTAGGTGTAGCACCAAATGCTGATCTATATGCTGTAAAAGTTCTTG p203

Fig. 2, continued

415 GCTTTGAATAACTCAATCGGCGTTGTAGGTGTAGCACCAAATGCTGATCTATATGCTGTAAAAGTTCTTG ZI120

412 GCTTTGAATAACTCAATTGGCGTTGTAGGTGTAGCACCAAATGCTGATCTATATGCTGTAAAAGTTCTTG EP63

418 GCTTTGAATAACTCAATCGGCGTTGTAGGTGTAGCACCAAATGCTGATCTATATGCTGTAAAAGTTCTTG ZI130

415 GCTTTGAATAACTCAATTGGCGTTGTAGGAGTAGCACCAAATGCTGATCTATATGCTGTAAAAGTTCTTG ZI132

367 GCACTTAATAACAGCATTGGTGTGGTAGGTGTTGCACCGAATGCTCAAATTTATGGAGTAAAAGTTCTAG ZI340

415 GCACTTAATAACAGCATTGGTGTTGTAGGTGTTGCACCTAATGCTCAAATTTATGGAGTAAAGGTACTAG ZI344

416 GCTCTAAATAATTCAATTGGTGTCATTGGTGTTGCACCGAATGCTGAATTATATGCTGTTAAAGTACTTG PD138

484 GGGCAAATGGTAGAGGAAGCATTGGAGGAATTGCACAAGGTTTAGAGTGGGCAGCTGCGAACAATATGCA EP655

470 GGGCAAATGGTAGAGGAAGCATTGGAGGAATTGCACAAGGTTTAGAGTGGGCAGCTGCGAACAATATGCA p203

485 GGGCAAATGGTAGAGGAAGCATTGGAGGAATTGCACAAGGTTTAGAGTGGGCAGCTGCGAACAATATGCA ZI120

482 GGGCAAATGGTAGAGGAAGCATTGGAGGAATTGCACAAGGTTTAGAGTGGGCAGCTGCGAACAATATGCA EP63

488 GGGCAAATGGTAGAGGAAGCATTGGAGGAATTGCACAAGGTTTAGAGTGGGCAGCTGCGAACAATATGCA ZI130

485 GGGCAAATGGTAGAGGAAGCATTGGCGGAATTGCACAAGGTTTAGAGTGGGCAGCTGCTAACAATATGCA ZI132

437 GAGCAAACGGTCGCGGAAGTGTGAGCGGTATTGCTCAGGGATTAGAGTGGGCCGCTACAAACAATATGGA ZI340

485 GAGCCAATGGTCGCGGAAGTGTAAGCGGTATTGCTCAAGGTTTAGAGTGGGCTGCTACAAATAATATGGA ZI344

486 GAGCAAATGGAAGCGGAAGTGTAAGTGGGATTGCTCAAGGTTTAGAGTGGGCGGCAACCAATAACATGCA PD138

554 CATAGCAAACTTGAGCCTTGGTAGCGATGCACCTAGCTCAACTCTTGAGCAGGCTGTTAATTACGCTACA EP655

540 CATAGCAAACTTGAGCCTTGGTAGCGATGCACCTAGCTCAACTCTTGAGCAGGCTGTTAATTACGCTACA p203

555 CATAGCAAACTTGAGCCTTGGTAGCGATGCACCTAGCTCAACTCTTGAGCAGGCTGTTAATTACGCTACA ZI120

552 CATAGCAAACTTGAGCCTTGGTAGCGATGCACCTAGCTCAACTCTTGAGCAGGCTGTTAATTATGCTACA EP63

558 CATAGCAAACTTGAGCCTTGGTAGCGATGCACCTAGCTCAACTCTTGAGCAGGCTGTTAATTACGCTACA ZI130

555 CATAGCAAACTTGAGCCTTGGTAGCGATGCACCTAGCTCAACTCTTGAGCAGGCTGTTAATTACGCTACA ZI132

507 TATTGCAAACTTAAGCCTAGGAAGTGACGCACCAAGCTCAACTCTTGAACAAGCTGTTAACTTTGCCACG ZI340

555 TATTGCAAACTTAAGCCTAGGAAGTGACGCGCCAAGCTCAACTCTTGAACAAGCTGTTAACTTTGCCACT ZI344

556 TATTGCGAACATGAGTCTCGGTAGTGATTTTCCTAGCTCTACACTTGAGCGTGCAGTCAACTATGCAACA PD138

624 AGTCGCGGTGTATTAGTTATTGCGGCTTCAGGTAATAACGGTTCAGGTAACGTTGGATATCCTGCACGTT EP655

610 AGTCGCGGTGTATTAGTTATTGCGGCTTCAGGTAATAACGGTTCAGGTAACGTTGGATATCCTGCACGTT p203

625 AGTCGCGGTGTATTAGTTATTGCGGCTTCAGGTAATAACGGTTCAGGTAACGTTGGATATCCTGCACGTT ZI120

Fig. 2, continued

```
622 AGTCGCGGTGTATTAGTTATTGCGGCTTCAGGTAATAACGGTTCAGGTAACGTTGGATATCCTGCACGTT EP63
628 AGTCGCGGTGTATTAGTTATTGCGGCTTCAGGTAATAACGGTTCAGGTAACGTTGGATATCCTGCACGTT ZI130
625 AGTCGCGGTGTATTAGTTATTGCGGCTTCAGGTAATAACGGTTCAGGTAACGTTGGATATCCTGCACGTT ZI132
577 AGCAGAGGTGTACTTGTTGTTGCAGCTTCAGGAAATAACGGGTCTGGAAACGTTGGCTTCCCTGCACGTT ZI340
625 AGCCGAGGTGTACTTGTTGTGGCAGCTTCAGGAAATAATGGATCTGGAAACGTTGGCTACCCTGCACGTT ZI344
626 AGCCGTGATGTACTAGTTATTGCAGCGACTGGTAATAACGGTTCTGGTTCAGTAGGCTATCCTGCTCGTT PD138
694 ATGCTAATGCAATGGCAGTAGGAGCAACCGATCAAAATAATAACCGTGCTAACTTCTCTCAATATGGTGC EP655
680 ATGCTAATGCAATGGCAGTAGGAGCAACCGATCAAAATAATAACCGTGCTAACTTCTCTCAATATGGTGC p203
695 ATGCTAATGCAATGGCAGTAGGAGCAACCGATCAAAATAATAACCGTGCTAACTTCTCTCAATATGGTGC ZI120
692 ATGCTAATGCAATGGCAGTAGGAGCAACCGATCAAAATAATAACCGTGCTAACTTCTCTCAATATGGTGC EP63
698 ATGCTAATGCAATGGCAGTAGGAGCAACCGATCAAAATAATAACCGTGCTAACTTCTCTCAATATGGTGC ZI130
695 ATGCTAATGCAATGGCAGTAGGAGCAACCGATCAAAATAATAACCGTGCTAACTTCTCTCAATACGGTGC ZI132
647 ACGCAAATGCAATGGCAGTTGGAGCAACAGATCAAAACAATAGACGCGCTAACTTTTCACAATATGGAGC ZI340
695 ATGCAAATGCAATGGCCGTTGGAGCAACAGATCAAAACAATAGGCGCGCTAACTTTTCACAATATGGAGC ZI344
696 ATGCAAACTCAATGGCTGTAGGAGCGACTGACCAAAACAACAGACGCGCAAACTTTTCTCAGTATGGTAC PD138
764 AGGACTTGATATCGTAGCTCCAGGTGTAGGCATTCAAAGTACGTATCCTGGTAACCGCTATGCGAGC--- EP655
750 AGGACTTGATATCGTAGCTCCAGGTGTAGGCATTCAAAGTACGTATCCTGGTAACCGCTATGCGAGC--- p203
765 AGGACTTGATATCGTAGCTCCAGGTGTAGGCATTCAAAGTACGTATCCTGGTAACCGCTATGCGAGC--- ZI120
762 AGGACTTGATATCGTAGCTCCAGGTGTAGGCATTCAAAGTACGTATCCTGGTAACCGCTATGCGAGC--- EP63
768 AGGACTTGATATCGTAGCTCCAGGTGTAGGCATTCAAAGTACGTATCCTGGTAACCGCTATGCGAGC--- ZI130
765 AGGACTTGATATCGTAGCTCCAGGTGTAGGCATTCAAAGTACGTACCCTGGTAACCGCTATGCGAGT--- ZI132
717 AGGTCTTGATATTGTAGCTCCTGGAGTAGGTGTACAAAGTACATATCCAGGCAATCGTTATGTAAGTATG ZI340
765 AGGACTTGATATTGTAGCTCCTGGAGTAGGGGTGCAAAGTACATATCCTGGTAACCGCTATGTAAGTATG ZI344
766 GGGAATTGACATCGTAGCACCTGGTGTTAACGTACAAAGTACGTATCCAGGTAACCGTTACGTGAGT--- PD138
831 ---------------CTAAA EP655
817 ---------------CTAAT p203
832 ---------------CTAAW ZI120
829 ---------------C EP63
```

Fig. 2 continued

```
835 ---------------CTAA                ZI130
832 ---------------CTAAT----GG         ZI132
787 AATAGTACATCTA-----------AG         ZI340
835 AATGATACATCTATGCTAACTCCAAA         ZI344
833 ---------------AT--------G         PD138
```

Fig. 2 continued

SUBTILASES

CROSS-REFERENCE TO RELATED APPLICATIONS

This application claims priority or the benefit under 35 U.S.C. 119 of Danish application nos. PA 2005 01366 and PA 2005 01155 filed Sep. 30, 2005 and Aug. 16, 2005, respectively and U.S. provisional application Nos. 60/722,517 and 60/709,403 filed Sep. 30, 2005 and Aug. 18, 2005, respectively, the contents of which are fully incorporated herein by reference.

SEQUENCES

This application contains the following sequences:

SEQ ID NO:1—DNA encoding subtilase from *Bacillus* sp. strain Zi344. Nucleic acids 337 to 1143 encodes the mature subtilase.

SEQ ID NO:2—Amino acid sequence of subtilase from *Bacillus* sp. strain Zi344. The mature subtilase is amino acids 113 to 381.

SEQ ID NO:3—DNA encoding subtilase from *Bacillus* sp. strain EP655. Nucleic acids 343 to 1149 encodes the mature subtilase.

SEQ ID NO:4—Amino acid sequence of subtilase from *Bacillus* sp. strain EP655. The mature subtilase is amino acids 115 to 383.

SEQ ID NO:5—DNA encoding subtilase from *Bacillus* sp. strain p203. Nucleic acids 343 to 1149 encodes the mature subtilase.

SEQ ID NO:6—Amino acid sequence of subtilase from *Bacillus* sp. strain p203. The mature subtilase is amino acids 115 to 383.

SEQ ID NO:7 to SEQ ID NO:27 are artificial primers.

SEQ ID NO:28—Partial DNA sequence encoding subtilase from *Bacillus* sp. strain EP63.

SEQ ID NO:29—Partial amino acid sequence of subtilase from *Bacillus* sp. strain EP63.

SEQ ID NO:30—Partial DNA sequence encoding subtilase from *Bacillus* sp. strain ZI120.

SEQ ID NO:31—Partial amino acid sequence of subtilase from *Bacillus* sp. strain ZI120.

SEQ ID NO:32—Partial DNA sequence encoding subtilase from *Bacillus* sp. strain ZI130.

SEQ ID NO:33—Partial amino acid sequence of subtilase from *Bacillus* sp. strain ZI130.

SEQ ID NO:34—Partial DNA sequence encoding subtilase from *Bacillus* sp. strain ZI132.

SEQ ID NO:35—Partial amino acid sequence of subtilase from *Bacillus* sp. strain ZI132.

SEQ ID NO:36—Partial DNA sequence encoding subtilase from *Bacillus* sp. strain ZI340.

SEQ ID NO:37—Partial amino acid sequence of subtilase from *Bacillus* sp. strain ZI340. The amino acid sequences of SEQ ID NO:29, 31, 33, 35 and 37 are mature subtilases where the C-terminals are truncated.

Deposited Microorganisms

The wild type strain referred to as p203 was deposited on 23 Jun. 2005 under the Budapest treaty at the Deutsche Sammlung von Mikroorganismen und Zellkulturen under the deposit number DSM 17419. The deposit contains the subtilase gene referred to as p203A herein, which is identical with SEQ ID NO:5.

FIELD OF THE INVENTION

The present invention relates to novel subtilases from wild-type strains of *Bacillus* and to methods of construction and production of these proteases. Further, the present invention relates to use of the claimed subtilases in detergents, such as a laundry detergent or an automatic dishwashing detergent.

BACKGROUND OF THE INVENTION

Enzymes have been used within the detergent industry as part of washing formulations for more than 30 years. Proteases are from a commercial perspective the most relevant enzyme in such formulations, but other enzymes including lipases, amylases, cellulases, hemicellulases or mixtures of enzymes are also often used.

The search for proteases with appropriate properties include both discovery of naturally occurring proteases, i.e. so called wild-type proteases but also alteration of well-known proteases by e.g. genetic manipulation of the nucleic acid sequence encoding said proteases. One family of proteases, which is often used in detergents, is the subtilases. This family has been further grouped into 6 different sub-groups (Siezen R. J. and Leunissen J. A. M., 1997, Protein Science, 6, 501-523). One of these sub-groups, the Subtilisin family was further divided into the subgroups of "true subtilisins (I-S1)", "high alkaline proteases (I-S2)" and "intracellular proteases". Siezen and Leunissen identified also some proteases of the subtilisin family, but not belonging to any of the subgroups. The true subtilisins include proteases such as subtilisin BPN' (BASBPN), subtilisin Carlsberg (ALCALASE®, NOVOZYMES A/S) (BLSCAR), mesentericopeptidase (BMSAMP) and subtilisin DY (BSSDY). The high alkaline proteases include proteases such as subtilisin 309 (SAVINASE®, NOVOZYMES A/S) (BLSAVI) subtilisin PB92 (BMLKP), subtilisin BL or BLAP (BLSUBL), subtilisin 147 (ESPERASE®, NOVOZYMES A/S), subtilisin Sendai (BSAPRS) and alkaline elastase YaB. Outside this grouping of the subtilisin family a further subtilisin subgroup was recently identified on the basis of the 3-D structure of its members, the TY145 like subtilisins. The TY145 like subtilisins include proteases such as TY145 (a subtilase from *Bacillus* sp. TY145, NCIMB 40339 described in WO 92/17577) (BSTY145), subtilisin TA41 (BSTA41), and subtilisin TA39 (BSTA39).

The PD138 type of protease was first described physicochemically in WO 93/18140 to Novo Nordisk A/S disclosing one strain producing this type of protease. In WO 93/18140, PD138 type of protease was described based on immunological cross reaction with a polyclonal rabbit antibody directed towards the purified protease. The primary structure of the protease was not disclosed. Later the *Bacillus* species producing this protease was taxonomically classified as *Bacillus gibsonii* (Nielsen et al. 1995). The type strain of *Bacillus gibsonii* is identical with the strain described in WO 93/18140. WO 2003/054184 and WO 2003/054185 disclose alkaline subtilases from strains of *Bacillus gibsonii.*

BRIEF DESCRIPTION OF THE INVENTION

The inventors have isolated novel proteases belonging to the PD138 like proteases subgroup of the subtilisin family that possess advantageous properties, such as improved performance in detergent at low temperature.

BRIEF DESCRIPTION OF DRAWINGS

FIG. 2. The alignment of the sequences from the PCR screening from FIG. 1.

DEFINITIONS

Figure 1:
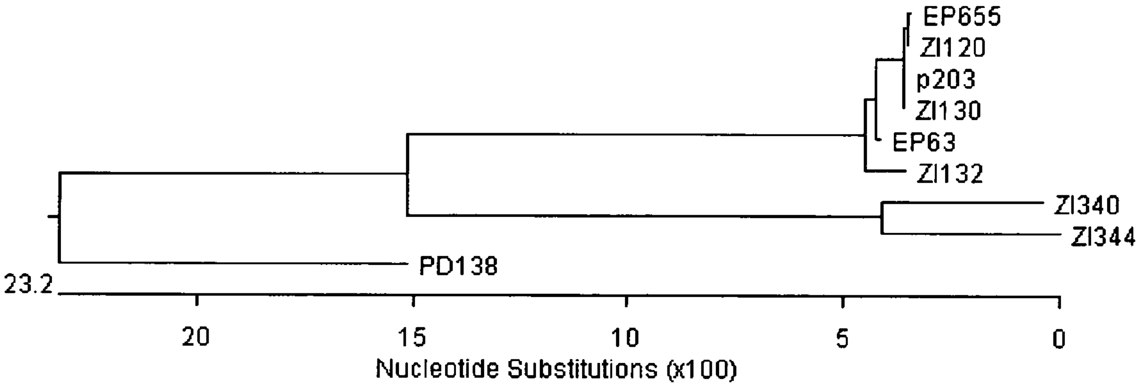
FIG. 1, Phylogenetic tree showing the relationship of the mature subtilase peptide sequences were constructed upon alignment with default settings in the ClustalV function of program MegAlign™ version 5.05 in DNAStar™ program package.

Prior to discussing this invention in further detail, the following terms and conventions will first be defined.

The term "subtilases" refer to a sub-group of serine proteases according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue.

The subtilases may be divided into 6 sub-divisions, i.e. the Subtilisin family, the Thermitase family, the Proteinase K family, the Lantibiotic peptidase family, the Kexin family and the Pyrolysin family.

The Subtilisin family (EC 3.4.21.62) may be further divided into 3 sub-groups, i.e. I-S1 ("true" subtilisins), I-S2 (highly alkaline proteases) and intracellular subtilisins. Definitions or grouping of enzymes may vary or change, however, in the context of the present invention the above division of subtilases into sub-division or sub-groups shall be understood as those described by Siezen et al., *Protein Engng.* 4 (1991) 719-737 and Siezen et al. *Protein Science* 6 (1997) 501-523.

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent subtilase" refers to a subtilase which is modified to create a subtilase variant.

"Homology" or "homologous to" is in the context of the present invention to be understood in its conventional meaning and the "homology" between two amino acid sequences should be determined by use of the "Similarity" defined by the GAP program from the University of Wisconsin Genetics Computer Group (UWGCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the UWGCG package version 9.1 with default setting for alignment parameters, comparison matrix, gap and gap extension penalties can also be applied using the following parameters: gap creation penalty=8 and gap extension penalty=8 and all other parameters kept at their default values. The output from the routine is besides the amino acid alignment the calculation of the "Percent Identity" and the "Similarity" between the two sequences. The numbers calculated using UWGCG package version 9.1 is slightly different from the version 8.

The term "position" is in the context of the present invention to be understood as the number of an amino acid in a peptide or polypeptide when counting from the N-terminal end of said peptide/polypeptide. The position numbers used in the present invention refer to different subtilases depending on which subgroup the subtilase belongs to.

DETAILED DESCRIPTION OF THE INVENTION

Selection of Strains Producing Novel Subtilisins

In the search for *Bacillus* strains producing novel subtilases we selected a number of strains, which based on 16S rDNA similarity was related to *Bacillus gibsonii*. The *Bacillus* strains P203, EP655, ZI344, EP63, ZI120, ZI130, ZI132 and ZI140 were fermented in a standard *Bacillus* fermentation medium (BP-X added 0.1 M $NaHCO_3$ to adjust pH to 9).

The immunochemical properties can be determined immunologically by cross-reaction identity tests. The identity test can be performed either by the well known ouchterlony double immuno diffusion procedure or by tandem crossed immunoelectro-phoresis according to N. H Axelsen, Handbook of immunoprecipitation-in-gel Techniques. Blackwell Scientific Publications (1983) chapters 5 &14. The terms "antigenic identity" and "partial antigenic identity" are described in the same book chapters 5, 19 and 20.

Culture fluids were analysed for protease activity using Alcalase™ as standard. Fluids with 10 CPU/L or more activity was included in the immunological analysis. The analysis included two different polyclonal rabbit antibodies; AB41 was antibody raised against the PD138 protease (WO 93/18140). The other antibody was AB65 raised against PD490 protease (Not published). The analysis gave two groups of proteases with a partial reaction against the AB41. One of these groups also has a partial reaction against AB65, whereas the other group reacted identical with AB65. A third group including PD138 gave identical reaction with AB41 and partial reaction with AB65.

PCR Screening

A part of the genes encoding the proteases which exhibited novel immunochemical properties as described above was amplified with a standard PCR reaction with PCR primers designed from available sequences, see Example 1.

Figure 2:
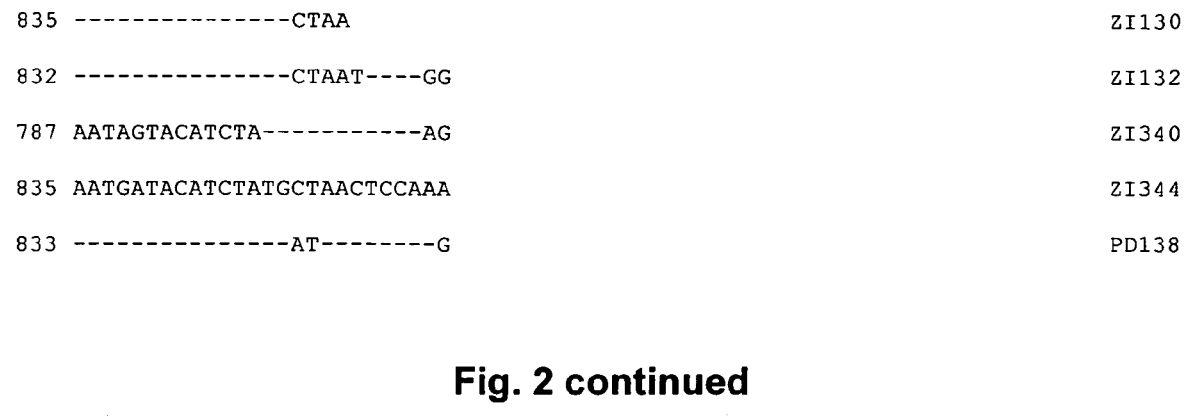

The nucleotide sequences were analysed with DNA STAR™, and based on nucleotide sequence diversity with PD138 as benchmark the novel groups identified with antibodies were confirmed. A phylogenetic tree based on the sequences from the PCR screening is presented in FIG. 1. A ClustalV alignment of the sequences from the PCR screening is shown in FIG. 2.

Cloning and Expression of Full Length Subtilase of the Invention

Inverse PCR

Inverse PCR was performed with specific DNA primers designed to complement the DNA sequence obtained from PCR product of the partial protease gene and chromosomal DNA extracted from the appropriate bacterial strain. Inverse PCR was made on the strains P203, EP655 and ZI344, whereas the strains EP63, ZI120, ZI130, ZI1342 and ZI140 were not further investigated. The inverse PCR products were nucleotide sequenced to obtain the region encoding the N and C terminal parts of the genes.

Production of Full Length Subtilase

The subtilase genes were amplified with specific primers with restriction sites in the 5' end of primers that allow gene fusion with the Savinase signal peptide of plasmid pDG268NeoMCS-PramyQ/PrcryIII/cryIIIAstab/Sav (U.S. Pat. No. 5,955,310). Protease positive colonies were selected and the coding sequence of the expressed enzyme from the expression construct was confirmed by DNA sequence analysis.

Subtilases of the Invention

The subtilases of the present invention include subtilases from the *Bacillus* strains ZI344, EP655, P203, EP63, ZI120, ZI130, ZI1342 and ZI140 as shown in SEQ ID NO:2, SEQ ID NO:4, SEQ ID NO:6, SEQ ID NO:29, SEQ ID NO:31, SEQ ID NO:33, SEQ ID NO:35 and SEQ ID NO:37 respectively. WO 2003/054184 disclose an alkaline protease from *Bacillus gibsonii*, DSM 14393 which has app. 85.9% amino acid sequence identity with ZI344 and app. 87% amino acid sequence identity with EP655 and P203. Further, the alkaline protease from *Bacillus gibsonii*, DSM 14393 has 88.2% identity with the partial sequence of the subtilases from ZI120 and ZI130 (SEQ ID NO:31 and 33); and 88.1%, 86.8% and 83.8% identity with the partial sequence of the subtilases from EP63, ZI132 and ZI340 (SEQ ID NO:29, 35 and 37) respectively.

The protease from *Bacillus gibsonii*, DSM 14393 is encoded by a nucleic acid sequence which is app. 75.5% identical with SEQ ID NO; 1 and app. 80.2% identical with SEQ ID NO's:3 and 5. The nucleic acid sequence encoding the protease from *Bacillus gibsonii*, DSM 14393 is 72.2%, 75.7%, 75.7%, 76.2% and 75.5% identical with the nucleic acid sequence encoding the mature part of the partial sequence of the subtilases from ZI340 (SEQ ID NO:36), ZI120 (SEQ ID NO:30), ZI130 (SEQ ID NO:32), EP63 (SEQ ID NO:28) and ZI132 (SEQ ID NO:34) respectively.

Thus, the subtilase of the present invention is at least 90% identical with SEQ ID NO:2, SEQ ID NO:4, SEQ ID NO:6, SEQ ID NO:29, SEQ ID NO:31, SEQ ID NO:33, SEQ ID NO:35 or SEQ ID NO:37. Preferably, said subtilase is at least 91% identical with SEQ ID NO:2, SEQ ID NO:4, SEQ ID NO:6, SEQ ID NO:29, SEQ ID NO:31, SEQ ID NO:33, SEQ ID NO:35 or SEQ ID NO:37, more preferably said subtilase is at least 92%, 93%, 94%, 95%, 96%, 97%, 98% or at least 99% identical with SEQ ID NO:2, SEQ ID NO:4, SEQ ID NO:6, SEQ ID NO:29, SEQ ID NO:31, SEQ ID NO:33, SEQ ID NO:35 or SEQ ID NO:37.

Correspondingly, the subtilases according to the present invention are encoded by an isolated nucleic acid sequence as shown in SEQ ID NO:1, SEQ ID NO:3, SEQ ID NO:5, SEQ ID NO:28, SEQ ID NO:30, SEQ ID NO:32, SEQ ID NO:34 or SEQ ID NO:36. Preferably, said nucleic acid sequence is at least 81% identical with SEQ ID NO:1, SEQ ID NO:3 or SEQ ID NO:5, more preferably said nucleic acid sequence is at least 82%, 83%, 84%, 85%, 86%, 87%, 88%, 89%, 90%, 91%, 92%, 93%, 94%, 95%, 96%, 97%, 98% or at least 99% identical with SEQ ID NO:1, SEQ ID NO:3, SEQ ID NO:5, SEQ ID NO:28, SEQ ID NO:30, SEQ ID NO:32, SEQ ID NO:34 or SEQ ID NO:36.

Further the isolated nucleic acid sequence encoding a subtilase of the invention hybridizes with a complementary strand of the nucleic acid sequence shown in SEQ ID NO:1, SEQ ID NO:3, SEQ ID NO:5, SEQ ID NO:28, SEQ ID NO:30, SEQ ID NO:32, SEQ ID NO:34 or SEQ ID NO:36 under low stringency conditions, at least under medium stringency conditions, at least under medium/high stringency conditions, at least under high stringency conditions, at least under very high stringency conditions as described below.

Hybridization

Suitable experimental conditions for determining hybridization between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6-13), $^{32}$P-dCTP-labeled (specific activity>$1\times10^{9}$ cpm/μg) probe for 12 hours at ca. 45° C. For various stringency conditions the filter is then washed twice for 30 minutes in 2×SSC, 0.5% SDS and at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Variants

Combined Modifications

The present invention also encompasses any of the above mentioned subtilase variants in combination with any other modification to the amino acid sequence thereof. Especially combinations with other modifications known in the art to provide improved properties to the enzyme are envisaged.

Such combinations comprise the positions: 222 (improves oxidation stability), 218 (improves thermal stability), substitutions in the $Ca^{2+}$-binding sites stabilizing the enzyme, e.g. position 76, and many other apparent from the prior art. In further embodiments a subtilase variant described herein may advantageously be combined with one or more modification(s) in any of the positions: 27, 36, 56, 76, 87, 95, 96, 97, 98, 99, 100, 101, 102, 103, 104, 120, 123, 167, 170, 206, 218, 222, 224, 232, 235, 236, 245, 248, 252 and 274 (BPN' numbering). The novel subtilases differ from the primary structure of BPN' by deletion at the following positions 36, 57 and 158 to 162. The novel subtilase are 6 amino acids shorter than BPN'.

Methods for Expression and Isolation of Proteins

To express an enzyme of the present invention the above mentioned host cells transformed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g. other polypeptides than the enzyme of the invention) which originates from the homologous cell where the enzyme of the invention is originally obtained from.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations, especially for automatic dish washing (ADW).

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Relase®, Alcalase®, Savinase®, Primase®, Everlase®, Esperase®, Ovozyme®, Coronase®, Polarzyme® and Kannase® (Novozymes A/S), Maxatase™, Maxacal™, Maxapem™, Properase™, Purafect™, Purafect OxP™, FN2™, FN3™, FN4™ and Purafect Prime™ (Genencor International, Inc.), BLAP X and BLAP S (Henkel).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas lipase*, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus lipase*, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially used amylases are Duramyl®, Termamyl®, Stainzyme®, Fungamyl® and BAN® (Novozymes A/S), Rapidase™, Purastar™ and Purastar OxAm™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* dis-closed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, Renozyme® and Carezyme™ (Novozymes A/S), Clazinase™, and Puradax HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes A/S).

Hemicellulases: Suitable hemicellulases include those of bacterial or fungal origin. Chemically modified or protein engineered mutants are included. Suitable hemicellulases include mannanase, lichenase, xylanase, arabinase, galactanase acetyl xylan esterase, glucorunidase, ferulic acid esterase, coumaric acid esterase and arabinofuranosidase as described in WO 95/35362. Suitable mannanases are described in WO 99/64619.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethyl-cellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

Typical powder detergent compositions for automated dishwashing include:

| 1) | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

| 2) | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dehydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

| 3) | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

| 4) | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

| 5) | |
|---|---|
| Nonionic surfactant | 1-7% |
| Sodium disilicate | 18-30% |
| Trisodium citrate | 10-24% |
| Sodium carbonate | 12-20% |
| Monopersulphate ($2KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

Powder and liquid dishwashing compositions with cleaning surfactant system typically include the following ingredients:

| 6) | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis(hydroxylethyl)amine N-oxide anhydrous and hexadecyl bis(hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

Non-aqueous liquid ADW compositions typically include the following ingredients:

| 7) | |
|---|---|
| Liquid nonionic surfactant e.g. alcohol ethoxylates | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

| 8) | |
|---|---|
| Liquid nonionic surfactant e.g. alcohol ethoxylates | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

Thixotropic liquid ADW compositions typically include the following ingredients:

| 9) | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

Liquid automatic dishwashing compositions typically include the following ingredients:

| 10) | |
|---|---|
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

Liquid ADW compositions containing protected bleach particles typically include the following ingredients:

| 11) | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", *Nature* 369, 1994, pp. 637-639.

Materials and Methods

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Example 1

Selection of Strains and Screening with Antibodies

In the search for *Bacillus* strains producing novel subtilases of the PD138 group we selected a number of strains, which based on 16S rDNA similarity was related to *Bacillus gibsonii*. A number of such *Bacillus* strains were fermented in a standard *Bacillus* fermentation medium (BP-X added 0.1 M NaHCO3 to adjust pH to 9).

The immunochemical properties can be determined immunologically by cross-reaction identity tests. The identity test can be performed either by the well known ouchterlony double immuno diffusion procedure or by tandem crossed immunoelectro-phoresis according to N. H Axelsen, Handbook of immunoprecipitation-in-gel Techniques. Blackwell Scientific Publications (1983) chapters 5 &14.

Culture fluids were analysed for protease activity using Alcalase™ as standard. Fluids with 10 CPU/L or more activity was included in the immunological analysis.

The analysis included two different antibodies; AB41 is a polyclonal rabbit antibody raised against the PD138 protease (WO 93/18140). The other antibody is AB65 raised against a bacterial subtilisin isolated from wild type *Bacillus* sp. PD490 (not published). The analysis revealed two novel groups of proteases with a partial reaction against the AB41. One of these groups also had a partial reaction against AB65 (EP655, ZI120, EP63, ZI130 and ZI132), whereas the other group reacted identical with AB65 (ZI344 and ZI430). A third group including the PD138 protease reacted identical with AB41 and partially identical with AB65.

TABLE 1

Different proteases and their reaction with two different antibodies.

| | Antibody | |
|---|---|---|
| Protease | AB41 | AB65 |
| PD138 | Identical | Partial |
| EP655 | Partial | Partial |
| ZI120 | Partial | Partial |
| EP63 | Partial | Partial |
| ZI130 | Partial | Partial |
| ZI132 | Partial | Partial |
| ZI344 | Partial | Identical |
| ZI340 | Partial | Identical |

A part of the subtilase gene was amplified with a standard PCR reaction with PCR primers: PD138A0 (SEQ ID NO:7)/PD138A2 (SEQ ID NO:9) gave a PCR product of about 900 nt; PD138A1 (SEQ ID NO:8)/PD138A2 (SEQ ID NO:9) gave a PCR product of about 450 nt; ZI344F (SEQ ID NO:10)/PD138A2 (SEQ ID NO:9) gave a PCR product of about 800 nt.

GAGGAGGCNGAGTTNGARGC (SEQ ID NO:7), the symbols for degenerations are: N for inosine and R for an equal mixture of A and G.

```
                                  (SEQ ID NO:8)
AGTTAGCAGATATAAATAATTCAA,

                                  (SEQ ID NO:9)
GTGGAGTAGCCATAGATGTACCA,

                                 (SEQ ID NO:10)
TGCAAACGAGGTTGAACAGG.
```

The PCR reaction that included 50 U/ml of Ampli-taq™ DNA polymerase (Perkin Elmer) 10× Amplitaq buffer (final concentration of $MgCl_2$ is 1.5 mM) 0.2 mM of each of the dNTPs (dATP, dCTP, dTTP and dGTP), 0.2 pmol/μl of the primers and 1 μl DNA template.

Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 1050 nucleotides. The PCR product was recovered by using Qiagen™ PCR purification kit as recommended by the manufacturer. The nucleotide sequences were determined by sequencing on an ABI PRISM™ DNA sequencer (Perkin Elmer).

The nucleotide sequences were analysed with DNA STAR™, and based on nucleotide sequence diversity with PD138 as benchmark the novel groups identified with antibodies were confirmed. A phylogenetic tree based on the sequences from the PCR screening is presented in FIG. 1. A ClustalV alignment of the sequences from the PCR screening is shown in FIG. 2.

Example 2

Production of Full Length Subtilases

Inverse PCR

Three digestions of the chromosomal DNA of the strains EP655, P203 and ZI344 were made using the restriction enzymes Mlu1, EcoR1 and Sac1. Upon digestion the DNA was separated from the restriction enzymes using Qiaquick™ PCR purification kit (art. 28106, Qiagen, Germany). The digestions were religated and subjected to a PCR reaction using primers (PCR primers SEQ ID NO's:11-16) designed to recognise the sequence of the PCR product already obtained. The following PCR protocols were applied: 94° C. 2 min 30 cycles of [94° C. for 15 s, 52° C. for 30 s, 72° C. for 2 min] 72° C. 20 min. In the PCR the amount of primer, DNA polymerase and buffer were the same as in Example 1. Alternatively a protocol with 94° C. 2 min 30 cycles of [94° C. for 15 s, 52° C. for 30 s, 68° C. for 3 min] 68° C. 20 min. and replacing Amplitaq® and Amplitaq® buffer with Long-template Taq Polymerase™ (Boehringer Mannheim) with the buffer supplied with the polymerase. The PCR reactions were analysed on 0.8% agarose gels stained with ethidium bromide. All PCR fragments were recovered and the nucleotide sequence was determined by using specific oligo primers different from those used in the PCR reaction (Sequencing primers SEQ ID NO's:17-22).

The following primers were used for obtaining the inverse PCR and sequencing:

```
Inverse PCR primers
P203A-PCR-R   (SEQ ID NO:11)  ACACGAGTAATACCCCAAGG

P203A-PCR-F   (SEQ ID NO:12)  GCTAATGCAATGGCAGTAGG

ZI344-PCR-R   (SEQ ID NO:13)  ACTCTTTGAATGCCCCAAGG

ZI344-PCR-F   (SEQ ID NO:14)  AGGTGTACTTGTTGTGGCAG

EP655-PCR-R   (SEQ ID NO:15)  AGTAATACCCCAAGGCACCG

EP655-PCR-F   (SEQ ID NO:16)  GCGGCTTCAGGTAATAACGG

Sequencing primers
P203A-seq-R   (SEQ ID NO:17)  CAACTCAACTGATAATACGG

P203A-seq-F   (SEQ ID NO:18)  TTCTCTCAATATGGTGCAGG

EP655-seq-R   (SEQ ID NO:19)  AATGCATCAACATCTTCAGG

EP655-seq-F   (SEQ ID NO:20)  GGATATCCTGCACGTTATGC

ZI344-seq-R   (SEQ ID NO:21)  AGTGCTTCTACATCCTCAGG

ZI344-seq-F   (SEQ ID NO:22)  AACGTTGGCTACCCTGCACG
```

Production of the Full Length Subtilase

To produce the subtilases of strains P203, EP655 and ZI344 the protease gene was amplified from chromosomal DNA of the wild type strains. For P203 chromosomal DNA of the strain DSM 17419 can be used. The protease gene was amplified as a app. 1200 nt (nucleotide) PCR product. For P203 primers P203A-Sac1/P203A-BamH1 for Zi344 primers ZI344-Sac1/ZI344-Mlu1 and for EP655 primers P203A-Sac1/EP655-MLu1 were used. Template DNA was chromosomal DNA of the respective wild type *Bacillus* strains.

Primers:

```
P203A-Sac1:
                                        (SEQ ID NO. 23)
TTATGGAGCTCCTAAAAATGAGGAGGCGACC

P203A-BamH1:
                                        (SEQ ID NO. 24)
TGTATGGATCCAAATAGAGACGAAACCGCCC

EP655-MLu1:
                                        (SEQ ID NO. 25)
GATTAACGCGTCTGCTCTTATCGACTAGCGG

ZI344-Sac1:
                                        (SEQ ID NO. 26)
TTATGGAGCTCGATCAATACAAGGAGGCGAC

ZI344-MIu1:
                                        (SEQ ID NO. 27)
GATTAACGCGTGTTCTTTTATCGTGTAGCTG

EP655-Sac1: use P203A-Sac1.
```

The PCR products were recovered using Qiaquick™ spin columns as recommended (Qiagen, Germany). The quality of the isolated template was evaluated by agarose gel electrophoresis. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of the correct size. The PCR products were digested with restriction enzymes Sac1 and Mlu1 and purified on GFX™ PCR and Gel Band Purification Kit (Amerham Biosciences).

The digested and purified PCR fragment was ligated to the Sac I and Mlu I digested plasmid pDG268NeoMCS-PramyQ/PrcryIII/cryIIIAstab/Sav (U.S. Pat. No. 5,955,310). The ligation mixture was used for transformation into *E. coli* TOP10F' (Invitrogen BV, The Netherlands) and several colonies were selected for miniprep (QIAprep® spin, QIAGEN GmbH, Germany). The purified plasmids were checked for insert before transformation into a strain of *Bacillus subtilis* derived from *B. subtilis* DN 1885 with disrupted apr, npr and pel genes (Diderichsen et al (1990), J. Bacteriol., 172, 4315-4321). The disruption was performed essentially as described in "*Bacillus subtilis* and other Gram-Positive Bacteria," American Society for Microbiology, p. 618, eds. A. L. Sonenshein, J. A. Hoch and Richard Losick (1993). Transformed cells were plated on 1% skim milk LB-PG agar plates, supplemented with 6 μg/ml chloramphenicol. The plated cells were incubated over night at 37° C. and protease containing colonies were identified by a surrounding clearing zone. Protease positive colonies were selected and the coding sequence of the expressed enzyme from the expression construct was confirmed by DNA sequence analysis.

Example 3

Purification and Characterisation

Purification

This procedure relates to purification of a 2 liter scale fermentation for the production of the subtilases of the invention in a *Bacillus* host cell.

Approximately 1.6 liters of fermentation broth are centrifuged at 5000 rpm for 35 minutes in 1 liter beakers. The supernatants are adjusted to pH 6.5 using 10% acetic acid and filtered on Seitz Supra® S100 filter plates.

The filtrates are concentrated to approximately 400 ml using an Amicon® CH2A UF unit equipped with an Amicon® S1Y10 UF cartridge. The UF concentrate is centrifuged and filtered prior to absorption at room temperature on a Bacitracin affinity column at pH 7. The protease is eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step are combined and applied to a 750 ml Sephadex® G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex® G25 column are combined and applied to a 150 ml CM Sepharose® CL 6B cation exchange column (5 cm dia.) equilibrated with a buffer containing 0.01 M dimethylglutaric acid, 0.2 M boric acid, and 0.002 M calcium chloride adjusted to pH 6.5.

The protease is eluted using a linear gradient of 0-0.1 M sodium chloride in 2 litres of the same buffer.

In a final purification step subtilase containing fractions from the CM Sepharos®, column are combined and concentrated in an Amicon® ultrafiltration cell equipped with a GR81PP membrane (from the Danish Sugar Factories Inc.).

Example 4

Stability of Subtilases

The stability of the subtilases of the invention can be evaluated in a standard Western European dishwashing tablet detergent without other enzymes than the experimentally added subtilases. The stability of the subtilases can be determined as the residual proteolytic activity after incubation of the subtilase in a detergent.

The formulation of a standard Western European Tablet detergent is defined as:

| Component | Percentage |
|---|---|
| Non-ionic surfactants | 0-10% |
| Foam regulators | 1-10% |
| Bleach (per-carbonate or per-borate) | 5-15% |
| Bleach activators (e.g. TAED) | 1-5% |
| Builders (e.g. carbonate, phosphate, tri-phosphate, Zeolite) | 50-75% |
| Polymers | 0-15% |
| Perfume, dye etc. | <1% |
| Water and fillers (e.g. sodium sulphate) | Balance |

Assay for Proteolytic Activity

The proteolytic activity is determined with casein as substrate. One Casein Protease Unit (CPU) is defined as the amount of protease liberating about 1 μM of primary amino groups (determined by comparison with a serine standard) per minute under standard conditions, i.e., incubation for about 30 minutes at about 25° C. at pH 9.5.

The proteolytic activity may also be determined by measuring the specific hydrolysis of succinyl-Ala-Ala-Pro-Leu-p-nitroanilide by said protease. The substrate is initially dissolved in for example, DMSO (Dimethyl Sulfoxide) and then diluted about 50 fold in about 0.035 M borate buffer, about pH 9.45. All protease samples may be diluted about 5-10 fold by the same borate buffer. Equal volumes of the substrate solution and sample are mixed in a well of an ELISA reader plate and read at about 405 nm at 25° C. All sample activities and concentrations are normalized to the standard protease solution activity and concentration, respectively.

A typical Western European tablet detergent for automated dishwashing is dissolved (5.5 g/L) in 9°dH water at ambient temperature maximum 30 minutes prior to start of analyses. Samples of subtilases are diluted to a concentration of 2-4 CPU/ml in Britten Robinson buffer (Britten Robinson buffer is: 40 mM Phosphate, 40 mM Acetate and 40 mM Borate) pH9.5. For the analyses every sample is divided and tested under two conditions: For the control the subtilase is diluted 1:9 in Britten Robinson buffer pH9.5 to a final volume of 1 ml. This sample is analysed immediately after dilution. For the detergent stability the subtilase sample is diluted 1:9 in detergent solution (detergent concentration in the stability test is 5 g/L) these samples are incubated at 55° C. for 30 minutes prior to analysis by addition of casein substrate.

The assay is started by addition of 2 volumes of casein substrate (casein substrate is 2 g of casein (Merck, Hammerstein grade) in 100 ml of Britten Robinson buffer pH 9.5, pH is re-adjusted to 9.5 when the casein is in solution). Samples are kept isothermic at 25° C. for 30 minutes. The reaction is stopped by addition of 5 ml TCA solution (TCA solution is 89.46 g of Tri-chloric acid, 149.48 g of Sodium acetate-tri-hydrate and 94.5 ml of glacial acetic acid in 2.5 L of deionised water). The samples are incubated at ambient temperature for at least 20 minutes and filtered through Whatman® paper filter no. 42.

400 μl of filtrate is mixed with 3 ml OPA reagent (OPA reagent is composed of: 3.812 g of borax, 0.08% EtOH, 0.2% DTT and 80 mg of o-phthal-dialdehyd in 100 ml water). Absorption at 340 nm is measured and CPU is calculated from the concentration of free amines on a standard of a solution of 0.01% L-serine (Merck art. 7769).

Example 5

Microtiter Egg Assay (MEA)

In this assay the digestion of denatured egg proteins by proteases in the presence of detergent can be followed in a 96-well microtiter plate. Heating of egg proteins produces visual changes and changes in physicochemical properties. The clear translucent material is transformed to a milky substance. This is partly due to sulfhydryl-disulfide interchange reactions of denatured proteins. For example, heating unmasks the sulfhydryl group of ovalbumin, and the unmasked groups form disulfide linkages. The digestion of the denatured egg proteins by proteases converts the milky egg solution to a more clear solution dependent on the ability of the enzymes to degrade egg proteins.

Procedure a) Prepare an egg solution by dissolving 200 mg egg powder (Sanovo International AS) in 93.7 mL, where the water hardness in adjusted to 16° dH. Denature the egg solution by increasing the temperature to 85° C. over an 8 minutes time period.

b) Dilute the subtilase enzyme to 320 nM in succinic acid buffer: 10 mM succinic acid+2 mM $CaCl_2$+0.02% non-ionic detergent (such as Brij35) adjusted to pH 6.5;

c) Prepare the detergent solution just before use by mixing 5 g detergent & 937.5 mL water (16°dH($Ca^{2+}$/$Mg^{2+}$ 4:1)). The dishwash detergent could be a typical Western Europe 2 in1 (use 8°dH) or 3 in1 tablet (use 16°dH) or an automatic dishwash powder product (use 8°dH). If the detergent already contains proteases, the detergent solution should be inactivated in a microwave oven at 85° C. for 5 minutes d) Add to each well in a 96 well microtiter plate: 10 μl of 320 nM enzyme solution (final concentration 20 nM)+150 μl detergent solution (final concentration 5 g/L, 16°d)+egg solution (320 μg egg protein/well).

Measure OD 410 nm immediately (time 0 minutes) on a spectrophotometer. Incubate exactly 20 minutes at 55° C. and then measure OD 410 nm again. Calculate ΔOD and compare the variants with the performance of a reference subtilase, such as Savinase® or Alcalase® from Novozymes A/S. The performance of the reference is set to ΔOD=100%.

By use of the above mentioned procedure the digestion of denatured egg proteins by the subtilase enzymes of the invention was compared with that of Savinase®. The results are presented in Table 1 as performance % of Savinase performance:

TABLE 1

| Savinase | Alcalase | EP655 | ZI344 | P203 |
|---|---|---|---|---|
| 100 | 10 | 211 | 230 | 212 |

The invention claimed is:

1. An isolated polypeptide having proteolytic activity which has an amino acid sequence which is at least 90% identical with the amino acid sequence of SEQ ID NO: 2.

2. The polypeptide of claim 1, which has an amino acid sequence which is at least 93% identical with the amino acid sequence of SEQ ID NO:2.

3. The polypeptide of claim 1, which has an amino acid sequence which is at least 95% identical with the amino acid sequence of SEQ ID NO:2.

4. The polypeptide of claim 1, which has an amino acid sequence which is at least 97% identical with the amino acid sequence of SEQ ID NO:2.

5. The polypeptide of claim 1, which comprises the amino acid sequence of SEQ ID NO:2.

6. The polypeptide of claim 1, wherein the polypeptide comprises the amino acid sequence of the mature subtilase from position 113 through position 381 of SEQ ID NO:2.

7. A detergent composition comprising a polypeptide having proteolytic activity according to claim 1 and a surfactant.

* * * * *

UNITED STATES PATENT AND TRADEMARK OFFICE

CERTIFICATE OF CORRECTION

PATENT NO. : 7,642,080 B2
APPLICATION NO. : 11/504743
DATED : January 5, 2010
INVENTOR(S) : Nielsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 37

<210> SEQ ID NO 1
<211> LENGTH: 1146
<212> TYPE: DNA
<213> ORGANISM: Bacillus sp. strain Zi344
<220> FEATURE:
<221> NAME/KEY: CDS
<222> LOCATION: (1)..(1146)

<400> SEQUENCE: 1

atg aat agg aaa gta gga aag tta gtt gca gga ttg gtt tgt gta acc      48
Met Asn Arg Lys Val Gly Lys Leu Val Ala Gly Leu Val Cys Val Thr
1               5                   10                  15
```

-continued

```
gcc tta tta aca gta aca acc gag gca tct gca gca gaa gaa aaa gta         96
Ala Leu Leu Thr Val Thr Thr Glu Ala Ser Ala Ala Glu Glu Lys Val
            20                  25                  30

aaa tat cta atc ggt ttt gaa aaa gaa gct gag ctt gaa gcc ttt gca        144
Lys Tyr Leu Ile Gly Phe Glu Lys Glu Ala Glu Leu Glu Ala Phe Ala
        35                  40                  45

aac gag gtt gaa cag gta ggc gtt ttc act aca gat gaa act cag cat        192
Asn Glu Val Glu Gln Val Gly Val Phe Thr Thr Asp Glu Thr Gln His
    50                  55                  60

gat gat gag acg att gat gtt gat att att tat gat tat gat tat att        240
Asp Asp Glu Thr Ile Asp Val Asp Ile Ile Tyr Asp Tyr Asp Tyr Ile
65                  70                  75                  80

cca gtc tta tca gta gag att gat cct gag gat gta gaa gca ctt agt        288
Pro Val Leu Ser Val Glu Ile Asp Pro Glu Asp Val Glu Ala Leu Ser
                85                  90                  95

caa gaa gaa ggc att gcc tat att gag gaa gac ttt gaa gta tct att        336
Gln Glu Glu Gly Ile Ala Tyr Ile Glu Glu Asp Phe Glu Val Ser Ile
            100                 105                 110

caa cag act gtt cct tgg ggc att caa aga gta caa gct cct gca gtt        384
Gln Gln Thr Val Pro Trp Gly Ile Gln Arg Val Gln Ala Pro Ala Val
        115                 120                 125

att aat cgt ggc att aat ggt agc ggg gtg cga gta gcg gtg ctt gat        432
Ile Asn Arg Gly Ile Asn Gly Ser Gly Val Arg Val Ala Val Leu Asp
    130                 135                 140

tca ggc att tcc tcc cat agt gat tta agc att tct ggt ggt gta agc        480
Ser Gly Ile Ser Ser His Ser Asp Leu Ser Ile Ser Gly Gly Val Ser
145                 150                 155                 160

ttt gtt cct ggt gaa cca acc ata gcc gat gga aat ggg cac ggg aca        528
Phe Val Pro Gly Glu Pro Thr Ile Ala Asp Gly Asn Gly His Gly Thr
                165                 170                 175

cac gta gct gga acg att gct gca ctt aat aac agc att ggt gtt gta        576
His Val Ala Gly Thr Ile Ala Ala Leu Asn Asn Ser Ile Gly Val Val
            180                 185                 190

ggt gtt gca cct aat gct caa att tat gga gta aag gta cta gga gcc        624
Gly Val Ala Pro Asn Ala Gln Ile Tyr Gly Val Lys Val Leu Gly Ala
        195                 200                 205

aat ggt cgc gga agt gta agc ggt att gct caa ggt tta gag tgg gct        672
Asn Gly Arg Gly Ser Val Ser Gly Ile Ala Gln Gly Leu Glu Trp Ala
    210                 215                 220

gct aca aat aat atg gat att gca aac tta agc cta gga agt gac gcg        720
Ala Thr Asn Asn Met Asp Ile Ala Asn Leu Ser Leu Gly Ser Asp Ala
225                 230                 235                 240

cca agc tca act ctt gaa caa gct gtt aac ttt gcc act agc cga ggt        768
Pro Ser Ser Thr Leu Glu Gln Ala Val Asn Phe Ala Thr Ser Arg Gly
                245                 250                 255

gta ctt gtt gtg gca gct tca gga aat aat gga tct gga aac gtt ggc        816
Val Leu Val Val Ala Ala Ser Gly Asn Asn Gly Ser Gly Asn Val Gly
            260                 265                 270

tac cct gca cgt tat gca aat gca atg gcc gtt gga gca aca gat caa        864
Tyr Pro Ala Arg Tyr Ala Asn Ala Met Ala Val Gly Ala Thr Asp Gln
        275                 280                 285

aac aat agg cgc gct aac ttt tca caa tat gga gca gga ctt gat att        912
Asn Asn Arg Arg Ala Asn Phe Ser Gln Tyr Gly Ala Gly Leu Asp Ile
    290                 295                 300

gta gct cct gga gta ggg gtg caa agt aca tat cct ggt aac cgc tat        960
Val Ala Pro Gly Val Gly Val Gln Ser Thr Tyr Pro Gly Asn Arg Tyr
305                 310                 315                 320

gta agt atg aat gga aca tca atg gca tct cca cac gtt gct ggt gct       1008
Val Ser Met Asn Gly Thr Ser Met Ala Ser Pro His Val Ala Gly Ala
                325                 330                 335
```

-continued

```
gct gct cta gtg aaa caa aga tat cca tca tgg agt aac act cag att      1056
Ala Ala Leu Val Lys Gln Arg Tyr Pro Ser Trp Ser Asn Thr Gln Ile
            340                 345                 350

cgt aat cat ttg aaa aat act gct acg aat ctt gga aac aca aat cag      1104
Arg Asn His Leu Lys Asn Thr Ala Thr Asn Leu Gly Asn Thr Asn Gln
        355                 360                 365

ttt ggt agt ggt ctt gta aat gca gac gca gct aca cga taa              1146
Phe Gly Ser Gly Leu Val Asn Ala Asp Ala Ala Thr Arg
    370                 375                 380


<210> SEQ ID NO 2
<211> LENGTH: 381
<212> TYPE: PRT
<213> ORGANISM: Bacillus sp. strain Zi344

<400> SEQUENCE: 2

Met Asn Arg Lys Val Gly Lys Leu Val Ala Gly Leu Val Cys Val Thr
1               5                   10                  15

Ala Leu Leu Thr Val Thr Thr Glu Ala Ser Ala Ala Glu Glu Lys Val
            20                  25                  30

Lys Tyr Leu Ile Gly Phe Glu Lys Glu Ala Glu Leu Glu Ala Phe Ala
        35                  40                  45

Asn Glu Val Glu Gln Val Gly Val Phe Thr Thr Asp Glu Thr Gln His
    50                  55                  60

Asp Asp Glu Thr Ile Asp Val Asp Ile Ile Tyr Asp Tyr Asp Tyr Ile
65                  70                  75                  80

Pro Val Leu Ser Val Glu Ile Asp Pro Glu Asp Val Glu Ala Leu Ser
                85                  90                  95

Gln Glu Glu Gly Ile Ala Tyr Ile Glu Glu Asp Phe Glu Val Ser Ile
            100                 105                 110

Gln Gln Thr Val Pro Trp Gly Ile Gln Arg Val Gln Ala Pro Ala Val
        115                 120                 125

Ile Asn Arg Gly Ile Asn Gly Ser Gly Val Arg Val Ala Val Leu Asp
    130                 135                 140

Ser Gly Ile Ser Ser His Ser Asp Leu Ser Ile Ser Gly Gly Val Ser
145                 150                 155                 160

Phe Val Pro Gly Glu Pro Thr Ile Ala Asp Gly Asn Gly His Gly Thr
                165                 170                 175

His Val Ala Gly Thr Ile Ala Ala Leu Asn Asn Ser Ile Gly Val Val
            180                 185                 190

Gly Val Ala Pro Asn Ala Gln Ile Tyr Gly Val Lys Val Leu Gly Ala
        195                 200                 205

Asn Gly Arg Gly Ser Val Ser Gly Ile Ala Gln Gly Leu Glu Trp Ala
    210                 215                 220

Ala Thr Asn Asn Met Asp Ile Ala Asn Leu Ser Leu Gly Ser Asp Ala
225                 230                 235                 240

Pro Ser Ser Thr Leu Glu Gln Ala Val Asn Phe Ala Thr Ser Arg Gly
                245                 250                 255

Val Leu Val Val Ala Ala Ser Gly Asn Asn Gly Ser Gly Asn Val Gly
            260                 265                 270

Tyr Pro Ala Arg Tyr Ala Asn Ala Met Ala Val Gly Ala Thr Asp Gln
        275                 280                 285

Asn Asn Arg Arg Ala Asn Phe Ser Gln Tyr Gly Ala Gly Leu Asp Ile
    290                 295                 300
```

-continued

```
Val Ala Pro Gly Val Gly Val Gln Ser Thr Tyr Pro Gly Asn Arg Tyr
305                 310                 315                 320

Val Ser Met Asn Gly Thr Ser Met Ala Ser Pro His Val Ala Gly Ala
                325                 330                 335

Ala Ala Leu Val Lys Gln Arg Tyr Pro Ser Trp Ser Asn Thr Gln Ile
            340                 345                 350

Arg Asn His Leu Lys Asn Thr Ala Thr Asn Leu Gly Asn Thr Asn Gln
        355                 360                 365

Phe Gly Ser Gly Leu Val Asn Ala Asp Ala Ala Thr Arg
    370                 375                 380


<210> SEQ ID NO 3
<211> LENGTH: 1152
<212> TYPE: DNA
<213> ORGANISM: Bacillus sp. strain EP655
<220> FEATURE:
<221> NAME/KEY: CDS
<222> LOCATION: (1)..(1152)

<400> SEQUENCE: 3

atg aaa aga aag att gga aaa ctt gtt gta gga ctt gtt tgt gta aca       48
Met Lys Arg Lys Ile Gly Lys Leu Val Val Gly Leu Val Cys Val Thr
1               5                   10                  15

gcc ctt gtt agt gtg aca gac tca gca tca gct gca gaa gaa aag gta       96
Ala Leu Val Ser Val Thr Asp Ser Ala Ser Ala Ala Glu Glu Lys Val
            20                  25                  30

aag tac cta att ggt ttt gaa aaa gaa gct gaa ctt gaa gct ttt aca      144
Lys Tyr Leu Ile Gly Phe Glu Lys Glu Ala Glu Leu Glu Ala Phe Thr
        35                  40                  45

gat gaa gtt gag cag gtt ggc gta ttc tct att gaa gaa gat cag caa      192
Asp Glu Val Glu Gln Val Gly Val Phe Ser Ile Glu Glu Asp Gln Gln
    50                  55                  60

aaa gaa gat tcg act gat att gat gta gac att att ttt gat tac gat      240
Lys Glu Asp Ser Thr Asp Ile Asp Val Asp Ile Ile Phe Asp Tyr Asp
65                  70                  75                  80

tat att ccc gta tta tca gtt gag ttg gac cct gaa gat gtt gat gca      288
Tyr Ile Pro Val Leu Ser Val Glu Leu Asp Pro Glu Asp Val Asp Ala
                85                  90                  95

tta agt gaa gaa gat gga atc gca tat att gaa gaa gac ttt gaa gta      336
Leu Ser Glu Glu Asp Gly Ile Ala Tyr Ile Glu Glu Asp Phe Glu Val
            100                 105                 110

tca atc cag caa tcg gtg cct tgg ggt att act cgt gta caa gct cca      384
Ser Ile Gln Gln Ser Val Pro Trp Gly Ile Thr Arg Val Gln Ala Pro
        115                 120                 125

gca gcg att aac cgt gga aca aat ggt tca gga gta aga gcg gct gta      432
Ala Ala Ile Asn Arg Gly Thr Asn Gly Ser Gly Val Arg Ala Ala Val
    130                 135                 140

ttg gat aca gga att tct aca cat agt gat tta aca att cgt ggt gga      480
Leu Asp Thr Gly Ile Ser Thr His Ser Asp Leu Thr Ile Arg Gly Gly
145                 150                 155                 160

gct agc ttc gtg cct ggt gaa cca aat aca tct gac tta aat ggc cat      528
Ala Ser Phe Val Pro Gly Glu Pro Asn Thr Ser Asp Leu Asn Gly His
                165                 170                 175

ggt acc cat gta gct gga aca att gca gct ttg aat aac tca atc ggc      576
Gly Thr His Val Ala Gly Thr Ile Ala Ala Leu Asn Asn Ser Ile Gly
            180                 185                 190

gtt gta ggt gta gca cca aat gct gat cta tat gct gta aaa gtt ctt      624
Val Val Gly Val Ala Pro Asn Ala Asp Leu Tyr Ala Val Lys Val Leu
        195                 200                 205

ggg gca aat ggt aga gga agc att gga gga att gca caa ggt tta gag      672
```

-continued

Gly Ala Asn Gly Arg Gly Ser Ile Gly Gly Ile Ala Gln Gly Leu Glu
    210                 215                 220 tgg gca gct gcg aac aat atg cac ata gca aac ttg agc ctt ggt agc      720
Trp Ala Ala Ala Asn Asn Met His Ile Ala Asn Leu Ser Leu Gly Ser
225                 230                 235                 240 gat gca cct agc tca act ctt gag cag gct gtt aat tac gct aca agt      768
Asp Ala Pro Ser Ser Thr Leu Glu Gln Ala Val Asn Tyr Ala Thr Ser
                245                 250                 255 cgc ggt gta tta gtt att gcg gct tca ggt aat aac ggt tca ggt aac      816
Arg Gly Val Leu Val Ile Ala Ala Ser Gly Asn Asn Gly Ser Gly Asn
            260                 265                 270 gtt gga tat cct gca cgt tat gct aat gca atg gca gta gga gca acc      864
Val Gly Tyr Pro Ala Arg Tyr Ala Asn Ala Met Ala Val Gly Ala Thr
        275                 280                 285 gat caa aat aat aac cgt gct aac ttc tct caa tat ggt gca gga ctt      912
Asp Gln Asn Asn Asn Arg Ala Asn Phe Ser Gln Tyr Gly Ala Gly Leu
    290                 295                 300 gat atc gta gct cca ggt gta ggc att caa agt acg tat cct ggt aac      960
Asp Ile Val Ala Pro Gly Val Gly Ile Gln Ser Thr Tyr Pro Gly Asn
305                 310                 315                 320 cgc tat gcg agc cta aat ggt aca tct atg gca act cct cac gtt gca     1008
Arg Tyr Ala Ser Leu Asn Gly Thr Ser Met Ala Thr Pro His Val Ala
                325                 330                 335 gga gcg gca gca ctt gta aaa caa cgc tat cct tct tgg agt gca tcg     1056
Gly Ala Ala Ala Leu Val Lys Gln Arg Tyr Pro Ser Trp Ser Ala Ser
            340                 345                 350 caa atc cgt aat cat ctg aaa aac aca tct acg aat cta gga agc tct     1104
Gln Ile Arg Asn His Leu Lys Asn Thr Ser Thr Asn Leu Gly Ser Ser
        355                 360                 365 aca tta tat ggt agt gga tta gta aac gca gat gcc gct agt cga taa     1152
Thr Leu Tyr Gly Ser Gly Leu Val Asn Ala Asp Ala Ala Ser Arg
    370                 375                 380

<210> SEQ ID NO 4
<211> LENGTH: 383
<212> TYPE: PRT
<213> ORGANISM: Bacillus sp. strain EP655

<400> SEQUENCE: 4

Met Lys Arg Lys Ile Gly Lys Leu Val Val Gly Leu Val Cys Val Thr
1               5                   10                  15

Ala Leu Val Ser Val Thr Asp Ser Ala Ser Ala Ala Glu Glu Lys Val
            20                  25                  30

Lys Tyr Leu Ile Gly Phe Glu Lys Glu Ala Glu Leu Glu Ala Phe Thr
        35                  40                  45

Asp Glu Val Glu Gln Val Gly Val Phe Ser Ile Glu Glu Asp Gln Gln
    50                  55                  60

Lys Glu Asp Ser Thr Asp Ile Asp Val Asp Ile Ile Phe Asp Tyr Asp
65                  70                  75                  80

Tyr Ile Pro Val Leu Ser Val Glu Leu Asp Pro Glu Asp Val Asp Ala
                85                  90                  95

Leu Ser Glu Glu Asp Gly Ile Ala Tyr Ile Glu Glu Asp Phe Glu Val
            100                 105                 110

Ser Ile Gln Gln Ser Val Pro Trp Gly Ile Thr Arg Val Gln Ala Pro
        115                 120                 125

Ala Ala Ile Asn Arg Gly Thr Asn Gly Ser Gly Val Arg Ala Ala Val
    130                 135                 140

-continued

```
Leu Asp Thr Gly Ile Ser Thr His Ser Asp Leu Thr Ile Arg Gly Gly
145                 150                 155                 160

Ala Ser Phe Val Pro Gly Glu Pro Asn Thr Ser Asp Leu Asn Gly His
                165                 170                 175

Gly Thr His Val Ala Gly Thr Ile Ala Ala Leu Asn Asn Ser Ile Gly
            180                 185                 190

Val Val Gly Val Ala Pro Asn Ala Asp Leu Tyr Ala Val Lys Val Leu
        195                 200                 205

Gly Ala Asn Gly Arg Gly Ser Ile Gly Gly Ile Ala Gln Gly Leu Glu
    210                 215                 220

Trp Ala Ala Ala Asn Asn Met His Ile Ala Asn Leu Ser Leu Gly Ser
225                 230                 235                 240

Asp Ala Pro Ser Ser Thr Leu Glu Gln Ala Val Asn Tyr Ala Thr Ser
                245                 250                 255

Arg Gly Val Leu Val Ile Ala Ala Ser Gly Asn Asn Gly Ser Gly Asn
            260                 265                 270

Val Gly Tyr Pro Ala Arg Tyr Ala Asn Ala Met Ala Val Gly Ala Thr
        275                 280                 285

Asp Gln Asn Asn Asn Arg Ala Asn Phe Ser Gln Tyr Gly Ala Gly Leu
    290                 295                 300

Asp Ile Val Ala Pro Gly Val Gly Ile Gln Ser Thr Tyr Pro Gly Asn
305                 310                 315                 320

Arg Tyr Ala Ser Leu Asn Gly Thr Ser Met Ala Thr Pro His Val Ala
                325                 330                 335

Gly Ala Ala Ala Leu Val Lys Gln Arg Tyr Pro Ser Trp Ser Ala Ser
            340                 345                 350

Gln Ile Arg Asn His Leu Lys Asn Thr Ser Thr Asn Leu Gly Ser Ser
        355                 360                 365

Thr Leu Tyr Gly Ser Gly Leu Val Asn Ala Asp Ala Ala Ser Arg
    370                 375                 380


<210> SEQ ID NO 5
<211> LENGTH: 1152
<212> TYPE: DNA
<213> ORGANISM: Bacillus sp. strain p203
<220> FEATURE:
<221> NAME/KEY: CDS
<222> LOCATION: (1)..(1152)

<400> SEQUENCE: 5

atg aaa aga aag att gga aaa ctt gtt gta gga ctt gtt tgt gta aca       48
Met Lys Arg Lys Ile Gly Lys Leu Val Val Gly Leu Val Cys Val Thr
1               5                   10                  15

gcc ctt gtt agt gtg aca gac tca gca tca gct gca gaa gaa aag gta       96
Ala Leu Val Ser Val Thr Asp Ser Ala Ser Ala Ala Glu Glu Lys Val
            20                  25                  30

aag tac cta att ggt ttt gaa aaa gaa gct gaa ctt gaa gct ttt aca      144
Lys Tyr Leu Ile Gly Phe Glu Lys Glu Ala Glu Leu Glu Ala Phe Thr
        35                  40                  45

gat gaa gtt gag cag gtt ggc gta ttc tct att gaa gaa gat cag caa      192
Asp Glu Val Glu Gln Val Gly Val Phe Ser Ile Glu Glu Asp Gln Gln
    50                  55                  60

aaa gaa gat tcg act gat att gat gta gac att att ttt gat tac gat      240
Lys Glu Asp Ser Thr Asp Ile Asp Val Asp Ile Ile Phe Asp Tyr Asp
65                  70                  75                  80

tat att ccc gta tta tca gtt gag ttg gac cct gaa gat gtt gat gca      288
Tyr Ile Pro Val Leu Ser Val Glu Leu Asp Pro Glu Asp Val Asp Ala
                85                  90                  95
```

-continued

```
tta agt gaa gaa gat gga atc gca tat att gaa gaa gac ttt gag gta      336
Leu Ser Glu Glu Asp Gly Ile Ala Tyr Ile Glu Glu Asp Phe Glu Val
            100                 105                 110

tca atc cag caa tcg gtg cct tgg ggt att act cgt gta caa gct cca      384
Ser Ile Gln Gln Ser Val Pro Trp Gly Ile Thr Arg Val Gln Ala Pro
        115                 120                 125

gca gcg att aac cgt gga aca aat ggt tca gga gta aga gtg gct gta      432
Ala Ala Ile Asn Arg Gly Thr Asn Gly Ser Gly Val Arg Val Ala Val
    130                 135                 140

ttg gat aca gga att tct aca cat agt gat tta aca att cgt ggt gga      480
Leu Asp Thr Gly Ile Ser Thr His Ser Asp Leu Thr Ile Arg Gly Gly
145                 150                 155                 160

gct agc ttc gtg cct ggt gaa cca aat aca tct gac tta aat ggc cat      528
Ala Ser Phe Val Pro Gly Glu Pro Asn Thr Ser Asp Leu Asn Gly His
                165                 170                 175

ggt acc cat gta gct gga aca att gca gct ttg aat aac tca atc ggc      576
Gly Thr His Val Ala Gly Thr Ile Ala Ala Leu Asn Asn Ser Ile Gly
            180                 185                 190

gtt gta ggt gta gca cca aat gct gat cta tat gct gta aaa gtt ctt      624
Val Val Gly Val Ala Pro Asn Ala Asp Leu Tyr Ala Val Lys Val Leu
        195                 200                 205

ggg gca aat ggt aga gga agc att gga gga att gca caa ggt tta ggg      672
Gly Ala Asn Gly Arg Gly Ser Ile Gly Gly Ile Ala Gln Gly Leu Gly
    210                 215                 220

tgg gca gct gcg aac aat atg cac ata gca aac ttg agc ctt ggt agc      720
Trp Ala Ala Ala Asn Asn Met His Ile Ala Asn Leu Ser Leu Gly Ser
225                 230                 235                 240

gat gca cct agc tca act ctt gag cag gct gtt aat tac gct aca agt      768
Asp Ala Pro Ser Ser Thr Leu Glu Gln Ala Val Asn Tyr Ala Thr Ser
                245                 250                 255

cgc ggt gta tta gtt att gcg gct tca ggt aat aac ggt tca ggt aac      816
Arg Gly Val Leu Val Ile Ala Ala Ser Gly Asn Asn Gly Ser Gly Asn
            260                 265                 270

gtt gga tat cct gca cgt tat gct aat gca atg gca gta gga gca acc      864
Val Gly Tyr Pro Ala Arg Tyr Ala Asn Ala Met Ala Val Gly Ala Thr
        275                 280                 285

gat caa aat aat aac cgt gct aac ttc tct caa tat ggt gca gga ctt      912
Asp Gln Asn Asn Asn Arg Ala Asn Phe Ser Gln Tyr Gly Ala Gly Leu
    290                 295                 300

gat atc gta gct cca ggt gta ggc att caa agt acg tat cct ggt aac      960
Asp Ile Val Ala Pro Gly Val Gly Ile Gln Ser Thr Tyr Pro Gly Asn
305                 310                 315                 320

cgc tat gcg agc cta aat ggt aca tct atg gca act cct cac gtt gca     1008
Arg Tyr Ala Ser Leu Asn Gly Thr Ser Met Ala Thr Pro His Val Ala
                325                 330                 335

gga gcg gca gca ctt gta aaa caa cgc tat cct tct tgg agt gca tcg     1056
Gly Ala Ala Ala Leu Val Lys Gln Arg Tyr Pro Ser Trp Ser Ala Ser
            340                 345                 350

caa atc cgt aat cat ctg aaa aac aca tct acg aat cta gga agc tct     1104
Gln Ile Arg Asn His Leu Lys Asn Thr Ser Thr Asn Leu Gly Ser Ser
        355                 360                 365

aca tta tat ggt agt gga tta gta aac gca gat gcc gct agt cga taa     1152
Thr Leu Tyr Gly Ser Gly Leu Val Asn Ala Asp Ala Ala Ser Arg
    370                 375                 380
```

<210> SEQ ID NO 6
<211> LENGTH: 383
<212> TYPE: PRT
<213> ORGANISM: Bacillus sp. strain p203

-continued

<400> SEQUENCE: 6

```
Met Lys Arg Lys Ile Gly Lys Leu Val Val Gly Leu Val Cys Val Thr
1               5                   10                  15

Ala Leu Val Ser Val Thr Asp Ser Ala Ser Ala Ala Glu Glu Lys Val
            20                  25                  30

Lys Tyr Leu Ile Gly Phe Glu Lys Glu Ala Glu Leu Glu Ala Phe Thr
        35                  40                  45

Asp Glu Val Glu Gln Val Gly Val Phe Ser Ile Glu Glu Asp Gln Gln
    50                  55                  60

Lys Glu Asp Ser Thr Asp Ile Asp Val Asp Ile Ile Phe Asp Tyr Asp
65                  70                  75                  80

Tyr Ile Pro Val Leu Ser Val Glu Leu Asp Pro Glu Asp Val Asp Ala
                85                  90                  95

Leu Ser Glu Glu Asp Gly Ile Ala Tyr Ile Glu Glu Asp Phe Glu Val
            100                 105                 110

Ser Ile Gln Gln Ser Val Pro Trp Gly Ile Thr Arg Val Gln Ala Pro
        115                 120                 125

Ala Ala Ile Asn Arg Gly Thr Asn Gly Ser Gly Val Arg Val Ala Val
    130                 135                 140

Leu Asp Thr Gly Ile Ser Thr His Ser Asp Leu Thr Ile Arg Gly Gly
145                 150                 155                 160

Ala Ser Phe Val Pro Gly Glu Pro Asn Thr Ser Asp Leu Asn Gly His
                165                 170                 175

Gly Thr His Val Ala Gly Thr Ile Ala Ala Leu Asn Asn Ser Ile Gly
            180                 185                 190

Val Val Gly Val Ala Pro Asn Ala Asp Leu Tyr Ala Val Lys Val Leu
        195                 200                 205

Gly Ala Asn Gly Arg Gly Ser Ile Gly Gly Ile Ala Gln Gly Leu Gly
    210                 215                 220

Trp Ala Ala Ala Asn Asn Met His Ile Ala Asn Leu Ser Leu Gly Ser
225                 230                 235                 240

Asp Ala Pro Ser Ser Thr Leu Glu Gln Ala Val Asn Tyr Ala Thr Ser
                245                 250                 255

Arg Gly Val Leu Val Ile Ala Ala Ser Gly Asn Asn Gly Ser Gly Asn
            260                 265                 270

Val Gly Tyr Pro Ala Arg Tyr Ala Asn Ala Met Ala Val Gly Ala Thr
        275                 280                 285

Asp Gln Asn Asn Asn Arg Ala Asn Phe Ser Gln Tyr Gly Ala Gly Leu
    290                 295                 300

Asp Ile Val Ala Pro Gly Val Gly Ile Gln Ser Thr Tyr Pro Gly Asn
305                 310                 315                 320

Arg Tyr Ala Ser Leu Asn Gly Thr Ser Met Ala Thr Pro His Val Ala
                325                 330                 335

Gly Ala Ala Ala Leu Val Lys Gln Arg Tyr Pro Ser Trp Ser Ala Ser
            340                 345                 350

Gln Ile Arg Asn His Leu Lys Asn Thr Ser Thr Asn Leu Gly Ser Ser
        355                 360                 365

Thr Leu Tyr Gly Ser Gly Leu Val Asn Ala Asp Ala Ala Ser Arg
    370                 375                 380
```

<210> SEQ ID NO 7
<211> LENGTH: 20
<212> TYPE: DNA
<213> ORGANISM: Artificial

-continued

<220> FEATURE:
<223> OTHER INFORMATION: Primer
<220> FEATURE:
<221> NAME/KEY: misc_feature
<222> LOCATION: (9)..(9)
<223> OTHER INFORMATION: n in position 9 is inosine
<220> FEATURE:
<221> NAME/KEY: misc_feature
<222> LOCATION: (15)..(15)
<223> OTHER INFORMATION: n in position 15 is inosine
<220> FEATURE:
<221> NAME/KEY: misc_feature
<222> LOCATION: (18)..(18)
<223> OTHER INFORMATION: r in position 18 is a 50/50 mixture of A and G

<400> SEQUENCE: 7
gaggaggcng agttngargc 20

<210> SEQ ID NO 8
<211> LENGTH: 24
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(24)

<400> SEQUENCE: 8
agttagcaga tataaataat tcaa 24

<210> SEQ ID NO 9
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(23)

<400> SEQUENCE: 9
gtggagtagc catagatgta cca 23

<210> SEQ ID NO 10
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 10
tgcaaacgag gttgaacagg 20

<210> SEQ ID NO 11
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 11
acacgagtaa taccccaagg 20

-continued

<210> SEQ ID NO 12
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 12
gctaatgcaa tggcagtagg 20

<210> SEQ ID NO 13
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 13
actctttgaa tgccccaagg 20

<210> SEQ ID NO 14
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 14
aggtgtactt gttgtggcag 20

<210> SEQ ID NO 15
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 15
agtaataccc caaggcaccg 20

<210> SEQ ID NO 16
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 16
gcggcttcag gtaataacgg 20

<210> SEQ ID NO 17
<211> LENGTH: 20
<212> TYPE: DNA

-continued

<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 17
caactcaact gataatacgg 20

<210> SEQ ID NO 18
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 18
ttctctcaat atggtgcagg 20

<210> SEQ ID NO 19
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 19
aatgcatcaa catcttcagg 20

<210> SEQ ID NO 20
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 20
ggatatcctg cacgttatgc 20

<210> SEQ ID NO 21
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(20)

<400> SEQUENCE: 21
agtgcttcta catcctcagg 20

<210> SEQ ID NO 22
<211> LENGTH: 20
<212> TYPE: DNA
<213> ORGANISM: Artificial
<220> FEATURE:
<223> OTHER INFORMATION: Primer
<220> FEATURE:

-continued

<221> NAME/KEY: misc_feature
<222> LOCATION: (1)..(20)

<400> SEQUENCE: 22
aacgttggct accctgcacg 20

<210> SEQ ID NO 23
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(31)

<400> SEQUENCE: 23
ttatggagct cctaaaaatg aggaggcgac c 31

<210> SEQ ID NO 24
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(31)

<400> SEQUENCE: 24
tgtatggatc caaatagaga cgaaaccgcc c 31

<210> SEQ ID NO 25
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(31)

<400> SEQUENCE: 25
gattaacgcg tctgctctta tcgactagcg g 31

<210> SEQ ID NO 26
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(31)

<400> SEQUENCE: 26
ttatggagct cgatcaatac aaggaggcga c 31

<210> SEQ ID NO 27
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(31)

<400> SEQUENCE: 27

-continued

```
gattaacgcg tgttctttta tcgtgtagct g                                31


<210> SEQ ID NO 28
<211> LENGTH: 828
<212> TYPE: DNA
<213> ORGANISM: Bacillus sp. strain EP63
<220> FEATURE:
<221> NAME/KEY: CDS
<222> LOCATION: (199)..(828)

<400> SEQUENCE: 28

gatgaagttg agcaggttgg cgtattctct attgaagaag atcagcaaaa agaagattcg     60

actgatattg atgtagacat tatttttgat tacgattata ttcccgtatt atcagttgaa    120

ttggatcctg aagatgttga tgcattaagt gaagaagatg gaatcgcata tattgaagaa    180

gactttgagg tatcaatt cag caa tcg gtg cct tgg ggt att act cgt gta      231
                    Gln Gln Ser Val Pro Trp Gly Ile Thr Arg Val
                    1               5                   10

caa gct cca gca gcg att aac cgt gga aca aat ggt tca gga gta aga      279
Gln Ala Pro Ala Ala Ile Asn Arg Gly Thr Asn Gly Ser Gly Val Arg
            15                  20                  25

gtg gct gta ttg gat aca gga att tct aca cat agt gat tta aca att      327
Val Ala Val Leu Asp Thr Gly Ile Ser Thr His Ser Asp Leu Thr Ile
        30                  35                  40

cgt ggt gga gct agc ttc gtg cct ggt gaa cca aat aca tct gac tta      375
Arg Gly Gly Ala Ser Phe Val Pro Gly Glu Pro Asn Thr Ser Asp Leu
    45                  50                  55

aat ggc cat ggt acc cat gta gcg gga aca att gca gct ttg aat aac      423
Asn Gly His Gly Thr His Val Ala Gly Thr Ile Ala Ala Leu Asn Asn
60                  65                  70                  75

tca att ggc gtt gta ggt gta gca cca aat gct gat cta tat gct gta      471
Ser Ile Gly Val Val Gly Val Ala Pro Asn Ala Asp Leu Tyr Ala Val
                80                  85                  90

aaa gtt ctt ggg gca aat ggt aga gga agc att gga gga att gca caa      519
Lys Val Leu Gly Ala Asn Gly Arg Gly Ser Ile Gly Gly Ile Ala Gln
            95                  100                 105

ggt tta gag tgg gca gct gcg aac aat atg cac ata gca aac ttg agc      567
Gly Leu Glu Trp Ala Ala Ala Asn Asn Met His Ile Ala Asn Leu Ser
        110                 115                 120

ctt ggt agc gat gca cct agc tca act ctt gag cag gct gtt aat tat      615
Leu Gly Ser Asp Ala Pro Ser Ser Thr Leu Glu Gln Ala Val Asn Tyr
    125                 130                 135

gct aca agt cgc ggt gta tta gtt att gcg gct tca ggt aat aac ggt      663
Ala Thr Ser Arg Gly Val Leu Val Ile Ala Ala Ser Gly Asn Asn Gly
140                 145                 150                 155

tca ggt aac gtt gga tat cct gca cgt tat gct aat gca atg gca gta      711
Ser Gly Asn Val Gly Tyr Pro Ala Arg Tyr Ala Asn Ala Met Ala Val
                160                 165                 170

gga gca acc gat caa aat aat aac cgt gct aac ttc tct caa tat ggt      759
Gly Ala Thr Asp Gln Asn Asn Asn Arg Ala Asn Phe Ser Gln Tyr Gly
            175                 180                 185

gca gga ctt gat atc gta gct cca ggt gta ggc att caa agt acg tat      807
Ala Gly Leu Asp Ile Val Ala Pro Gly Val Gly Ile Gln Ser Thr Tyr
        190                 195                 200

cct ggt aac cgc tat gcg agc                                          828
Pro Gly Asn Arg Tyr Ala Ser
    205                 210


<210> SEQ ID NO 29
<211> LENGTH: 210
```

-continued

<212> TYPE: PRT
<213> ORGANISM: Bacillus sp. strain EP63

<400> SEQUENCE: 29

Gln Gln Ser Val Pro Trp Gly Ile Thr Arg Val Gln Ala Pro Ala Ala
1 5 10 15

Ile Asn Arg Gly Thr Asn Gly Ser Gly Val Arg Val Ala Val Leu Asp
20 25 30

Thr Gly Ile Ser Thr His Ser Asp Leu Thr Ile Arg Gly Gly Ala Ser
35 40 45

Phe Val Pro Gly Glu Pro Asn Thr Ser Asp Leu Asn Gly His Gly Thr
50 55 60

His Val Ala Gly Thr Ile Ala Ala Leu Asn Asn Ser Ile Gly Val Val
65 70 75 80

Gly Val Ala Pro Asn Ala Asp Leu Tyr Ala Val Lys Val Leu Gly Ala
85 90 95

Asn Gly Arg Gly Ser Ile Gly Gly Ile Ala Gln Gly Leu Glu Trp Ala
100 105 110

Ala Ala Asn Asn Met His Ile Ala Asn Leu Ser Leu Gly Ser Asp Ala
115 120 125

Pro Ser Ser Thr Leu Glu Gln Ala Val Asn Tyr Ala Thr Ser Arg Gly
130 135 140

Val Leu Val Ile Ala Ala Ser Gly Asn Asn Gly Ser Gly Asn Val Gly
145 150 155 160

Tyr Pro Ala Arg Tyr Ala Asn Ala Met Ala Val Gly Ala Thr Asp Gln
165 170 175

Asn Asn Asn Arg Ala Asn Phe Ser Gln Tyr Gly Ala Gly Leu Asp Ile
180 185 190

Val Ala Pro Gly Val Gly Ile Gln Ser Thr Tyr Pro Gly Asn Arg Tyr
195 200 205

Ala Ser
210

<210> SEQ ID NO 30
<211> LENGTH: 834
<212> TYPE: DNA
<213> ORGANISM: Bacillus sp. strain ZI120
<220> FEATURE:
<221> NAME/KEY: CDS
<222> LOCATION: (202)..(834)

<400> SEQUENCE: 30
acagatgaag ttgagcaggt tggcgtattc tctattgaag aagatcagca aaaagaagat 60
tcgactgata ttgatgtaga cattattttt gattacgatt atattcccgt attatcagtt 120
gagttggacc ctgaagatgt tgatgcatta agtgaagaag atggaatcgc atatattgaa 180
gaagactttg aagtatcaat c cag caa tcg gtg cct tgg ggt att act cgt 231
Gln Gln Ser Val Pro Trp Gly Ile Thr Arg
1 5 10 gta caa gct cca gca gcg att aac cgt gga aca aat ggt tca gga gta 279
Val Gln Ala Pro Ala Ala Ile Asn Arg Gly Thr Asn Gly Ser Gly Val
15 20 25 aga gtg gct gta ttg gat aca gga att tct aca cat agt gat tta aca 327
Arg Val Ala Val Leu Asp Thr Gly Ile Ser Thr His Ser Asp Leu Thr
30 35 40 att cgt ggt gga gct agc ttc gtg cct ggt gaa cca aat aca tct gac 375
Ile Arg Gly Gly Ala Ser Phe Val Pro Gly Glu Pro Asn Thr Ser Asp
45 50 55

-continued

```
tta aat ggc cat ggt acc cat gta gct gga aca att gca gct ttg aat      423
Leu Asn Gly His Gly Thr His Val Ala Gly Thr Ile Ala Ala Leu Asn
    60                  65                  70

aac tca atc ggc gtt gta ggt gta gca cca aat gct gat cta tat gct      471
Asn Ser Ile Gly Val Val Gly Val Ala Pro Asn Ala Asp Leu Tyr Ala
75                  80                  85                  90

gta aaa gtt ctt ggg gca aat ggt aga gga agc att gga gga att gca      519
Val Lys Val Leu Gly Ala Asn Gly Arg Gly Ser Ile Gly Gly Ile Ala
                95                  100                 105

caa ggt tta gag tgg gca gct gcg aac aat atg cac ata gca aac ttg      567
Gln Gly Leu Glu Trp Ala Ala Ala Asn Asn Met His Ile Ala Asn Leu
            110                 115                 120

agc ctt ggt agc gat gca cct agc tca act ctt gag cag gct gtt aat      615
Ser Leu Gly Ser Asp Ala Pro Ser Ser Thr Leu Glu Gln Ala Val Asn
        125                 130                 135

tac gct aca agt cgc ggt gta tta gtt att gcg gct tca ggt aat aac      663
Tyr Ala Thr Ser Arg Gly Val Leu Val Ile Ala Ala Ser Gly Asn Asn
    140                 145                 150

ggt tca ggt aac gtt gga tat cct gca cgt tat gct aat gca atg gca      711
Gly Ser Gly Asn Val Gly Tyr Pro Ala Arg Tyr Ala Asn Ala Met Ala
155                 160                 165                 170

gta gga gca acc gat caa aat aat aac cgt gct aac ttc tct caa tat      759
Val Gly Ala Thr Asp Gln Asn Asn Asn Arg Ala Asn Phe Ser Gln Tyr
                175                 180                 185

ggt gca gga ctt gat atc gta gct cca ggt gta ggc att caa agt acg      807
Gly Ala Gly Leu Asp Ile Val Ala Pro Gly Val Gly Ile Gln Ser Thr
            190                 195                 200

tat cct ggt aac cgc tat gcg agc cta                                  834
Tyr Pro Gly Asn Arg Tyr Ala Ser Leu
        205                 210


<210> SEQ ID NO 31
<211> LENGTH: 211
<212> TYPE: PRT
<213> ORGANISM: Bacillus sp. strain ZI120

<400> SEQUENCE: 31

Gln Gln Ser Val Pro Trp Gly Ile Thr Arg Val Gln Ala Pro Ala Ala
1               5                   10                  15

Ile Asn Arg Gly Thr Asn Gly Ser Gly Val Arg Val Ala Val Leu Asp
            20                  25                  30

Thr Gly Ile Ser Thr His Ser Asp Leu Thr Ile Arg Gly Gly Ala Ser
        35                  40                  45

Phe Val Pro Gly Glu Pro Asn Thr Ser Asp Leu Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Asp Leu Tyr Ala Val Lys Val Leu Gly Ala
                85                  90                  95

Asn Gly Arg Gly Ser Ile Gly Gly Ile Ala Gln Gly Leu Glu Trp Ala
            100                 105                 110

Ala Ala Asn Asn Met His Ile Ala Asn Leu Ser Leu Gly Ser Asp Ala
        115                 120                 125

Pro Ser Ser Thr Leu Glu Gln Ala Val Asn Tyr Ala Thr Ser Arg Gly
    130                 135                 140

Val Leu Val Ile Ala Ala Ser Gly Asn Asn Gly Ser Gly Asn Val Gly
145                 150                 155                 160
```

-continued

```
Tyr Pro Ala Arg Tyr Ala Asn Ala Met Ala Val Gly Ala Thr Asp Gln
                165                 170                 175

Asn Asn Asn Arg Ala Asn Phe Ser Gln Tyr Gly Ala Gly Leu Asp Ile
            180                 185                 190

Val Ala Pro Gly Val Gly Ile Gln Ser Thr Tyr Pro Gly Asn Arg Tyr
        195                 200                 205

Ala Ser Leu
    210


<210> SEQ ID NO 32
<211> LENGTH: 837
<212> TYPE: DNA
<213> ORGANISM: Bacillus sp. strain ZI130
<220> FEATURE:
<221> NAME/KEY: CDS
<222> LOCATION: (205)..(837)

<400> SEQUENCE: 32

tttacagatg aagttgagca ggttggcgta ttctctattg aagaagatca gcaaaaagaa      60

gattcgactg atattgatgt agacattatt tttgattacg attatattcc cgtattatca     120

gttgagttgg accctgaaga tgttgatgca ttaagtgaag aagatggaat cgcatatatt     180

gaagaagact ttgaggtatc aatc cag caa tcg gtg cct tgg ggt att act        231
                           Gln Gln Ser Val Pro Trp Gly Ile Thr
                           1               5

cgt gta caa gct cca gca gcg att aac cgt gga aca aat ggt tca gga       279
Arg Val Gln Ala Pro Ala Ala Ile Asn Arg Gly Thr Asn Gly Ser Gly
10                  15                  20                  25

gta aga gtg gct gta ttg gat aca gga att tct aca cat agt gat tta       327
Val Arg Val Ala Val Leu Asp Thr Gly Ile Ser Thr His Ser Asp Leu
                30                  35                  40

aca att cgt ggt gga gct agc ttc gtg cct ggt gaa cca aat aca tct       375
Thr Ile Arg Gly Gly Ala Ser Phe Val Pro Gly Glu Pro Asn Thr Ser
            45                  50                  55

gac tta aat ggc cat ggt acc cat gta gct gga aca att gca gct ttg       423
Asp Leu Asn Gly His Gly Thr His Val Ala Gly Thr Ile Ala Ala Leu
        60                  65                  70

aat aac tca atc ggc gtt gta ggt gta gca cca aat gct gat cta tat       471
Asn Asn Ser Ile Gly Val Val Gly Val Ala Pro Asn Ala Asp Leu Tyr
    75                  80                  85

gct gta aaa gtt ctt ggg gca aat ggt aga gga agc att gga gga att       519
Ala Val Lys Val Leu Gly Ala Asn Gly Arg Gly Ser Ile Gly Gly Ile
90                  95                  100                 105

gca caa ggt tta gag tgg gca gct gcg aac aat atg cac ata gca aac       567
Ala Gln Gly Leu Glu Trp Ala Ala Ala Asn Asn Met His Ile Ala Asn
                110                 115                 120

ttg agc ctt ggt agc gat gca cct agc tca act ctt gag cag gct gtt       615
Leu Ser Leu Gly Ser Asp Ala Pro Ser Ser Thr Leu Glu Gln Ala Val
            125                 130                 135

aat tac gct aca agt cgc ggt gta tta gtt att gcg gct tca ggt aat       663
Asn Tyr Ala Thr Ser Arg Gly Val Leu Val Ile Ala Ala Ser Gly Asn
        140                 145                 150

aac ggt tca ggt aac gtt gga tat cct gca cgt tat gct aat gca atg       711
Asn Gly Ser Gly Asn Val Gly Tyr Pro Ala Arg Tyr Ala Asn Ala Met
    155                 160                 165

gca gta gga gca acc gat caa aat aat aac cgt gct aac ttc tct caa       759
Ala Val Gly Ala Thr Asp Gln Asn Asn Asn Arg Ala Asn Phe Ser Gln
170                 175                 180                 185
```

-continued

```
tat ggt gca gga ctt gat atc gta gct cca ggt gta ggc att caa agt      807
Tyr Gly Ala Gly Leu Asp Ile Val Ala Pro Gly Val Gly Ile Gln Ser
                190                 195                 200

acg tat cct ggt aac cgc tat gcg agc cta                              837
Thr Tyr Pro Gly Asn Arg Tyr Ala Ser Leu
            205                 210


<210> SEQ ID NO 33
<211> LENGTH: 211
<212> TYPE: PRT
<213> ORGANISM: Bacillus sp. strain ZI130

<400> SEQUENCE: 33

Gln Gln Ser Val Pro Trp Gly Ile Thr Arg Val Gln Ala Pro Ala Ala
1               5                   10                  15

Ile Asn Arg Gly Thr Asn Gly Ser Gly Val Arg Val Ala Val Leu Asp
            20                  25                  30

Thr Gly Ile Ser Thr His Ser Asp Leu Thr Ile Arg Gly Gly Ala Ser
        35                  40                  45

Phe Val Pro Gly Glu Pro Asn Thr Ser Asp Leu Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Asp Leu Tyr Ala Val Lys Val Leu Gly Ala
                85                  90                  95

Asn Gly Arg Gly Ser Ile Gly Gly Ile Ala Gln Gly Leu Glu Trp Ala
            100                 105                 110

Ala Ala Asn Asn Met His Ile Ala Asn Leu Ser Leu Gly Ser Asp Ala
        115                 120                 125

Pro Ser Ser Thr Leu Glu Gln Ala Val Asn Tyr Ala Thr Ser Arg Gly
    130                 135                 140

Val Leu Val Ile Ala Ala Ser Gly Asn Asn Gly Ser Gly Asn Val Gly
145                 150                 155                 160

Tyr Pro Ala Arg Tyr Ala Asn Ala Met Ala Val Gly Ala Thr Asp Gln
                165                 170                 175

Asn Asn Asn Arg Ala Asn Phe Ser Gln Tyr Gly Ala Gly Leu Asp Ile
            180                 185                 190

Val Ala Pro Gly Val Gly Ile Gln Ser Thr Tyr Pro Gly Asn Arg Tyr
        195                 200                 205

Ala Ser Leu
    210


<210> SEQ ID NO 34
<211> LENGTH: 837
<212> TYPE: DNA
<213> ORGANISM: Bacillus sp. strain ZI132
<220> FEATURE:
<221> NAME/KEY: CDS
<222> LOCATION: (202)..(837)

<400> SEQUENCE: 34

acagatgaag ttgaacaggt tggcgtattc tctattgaag aagatcagca aaaagaagat     60

tcgactgata ttgatgtaga cattattttt gattacgatt atattcccgt attatcagtt    120

gaattggatc ctgaagatgt tgatgcatta agtgaagaag atggaatcgc atatattgaa    180

gaagactttg aggtatcaat t cag caa tcg gtg cct tgg ggt att aat cgt      231
                        Gln Gln Ser Val Pro Trp Gly Ile Asn Arg
                        1               5                   10

gta caa gct cca aca gcg att aac cgt gga aca aat ggt tca gga gta      279
```

-continued

```
Val Gln Ala Pro Thr Ala Ile Asn Arg Gly Thr Asn Gly Ser Gly Val
                15                  20                  25

aga gtg gct gta ttg gat aca gga att tct aca cat agt gat tta aca      327
Arg Val Ala Val Leu Asp Thr Gly Ile Ser Thr His Ser Asp Leu Thr
            30                  35                  40

att cgt ggt gga gct agc ttc gtg cct ggt gaa cca aat aca tct gac      375
Ile Arg Gly Gly Ala Ser Phe Val Pro Gly Glu Pro Asn Thr Ser Asp
        45                  50                  55

tta aat ggc cat ggt act cat gta gcg gga aca att gca gct ttg aat      423
Leu Asn Gly His Gly Thr His Val Ala Gly Thr Ile Ala Ala Leu Asn
    60                  65                  70

aac tca att ggc gtt gta gga gta gca cca aat gct gat cta tat gct      471
Asn Ser Ile Gly Val Val Gly Val Ala Pro Asn Ala Asp Leu Tyr Ala
75                  80                  85                  90

gta aaa gtt ctt ggg gca aat ggt aga gga agc att ggc gga att gca      519
Val Lys Val Leu Gly Ala Asn Gly Arg Gly Ser Ile Gly Gly Ile Ala
                95                  100                 105

caa ggt tta gag tgg gca gct gct aac aat atg cac ata gca aac ttg      567
Gln Gly Leu Glu Trp Ala Ala Ala Asn Asn Met His Ile Ala Asn Leu
            110                 115                 120

agc ctt ggt agc gat gca cct agc tca act ctt gag cag gct gtt aat      615
Ser Leu Gly Ser Asp Ala Pro Ser Ser Thr Leu Glu Gln Ala Val Asn
        125                 130                 135

tac gct aca agt cgc ggt gta tta gtt att gcg gct tca ggt aat aac      663
Tyr Ala Thr Ser Arg Gly Val Leu Val Ile Ala Ala Ser Gly Asn Asn
    140                 145                 150

ggt tca ggt aac gtt gga tat cct gca cgt tat gct aat gca atg gca      711
Gly Ser Gly Asn Val Gly Tyr Pro Ala Arg Tyr Ala Asn Ala Met Ala
155                 160                 165                 170

gta gga gca acc gat caa aat aat aac cgt gct aac ttc tct caa tac      759
Val Gly Ala Thr Asp Gln Asn Asn Asn Arg Ala Asn Phe Ser Gln Tyr
                175                 180                 185

ggt gca gga ctt gat atc gta gct cca ggt gta ggc att caa agt acg      807
Gly Ala Gly Leu Asp Ile Val Ala Pro Gly Val Gly Ile Gln Ser Thr
            190                 195                 200

tac cct ggt aac cgc tat gcg agt cta atg                              837
Tyr Pro Gly Asn Arg Tyr Ala Ser Leu Met
        205                 210


<210> SEQ ID NO 35
<211> LENGTH: 212
<212> TYPE: PRT
<213> ORGANISM: Bacillus sp. strain ZI132

<400> SEQUENCE: 35

Gln Gln Ser Val Pro Trp Gly Ile Asn Arg Val Gln Ala Pro Thr Ala
1               5                   10                  15

Ile Asn Arg Gly Thr Asn Gly Ser Gly Val Arg Val Ala Val Leu Asp
            20                  25                  30

Thr Gly Ile Ser Thr His Ser Asp Leu Thr Ile Arg Gly Gly Ala Ser
        35                  40                  45

Phe Val Pro Gly Glu Pro Asn Thr Ser Asp Leu Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Asp Leu Tyr Ala Val Lys Val Leu Gly Ala
                85                  90                  95

Asn Gly Arg Gly Ser Ile Gly Gly Ile Ala Gln Gly Leu Glu Trp Ala
            100                 105                 110
```

-continued

```
Ala Ala Asn Asn Met His Ile Ala Asn Leu Ser Leu Gly Ser Asp Ala
        115                 120                 125

Pro Ser Ser Thr Leu Glu Gln Ala Val Asn Tyr Ala Thr Ser Arg Gly
    130                 135                 140

Val Leu Val Ile Ala Ala Ser Gly Asn Asn Gly Ser Gly Asn Val Gly
145                 150                 155                 160

Tyr Pro Ala Arg Tyr Ala Asn Ala Met Ala Val Gly Ala Thr Asp Gln
                165                 170                 175

Asn Asn Asn Arg Ala Asn Phe Ser Gln Tyr Gly Ala Gly Leu Asp Ile
            180                 185                 190

Val Ala Pro Gly Val Gly Ile Gln Ser Thr Tyr Pro Gly Asn Arg Tyr
        195                 200                 205

Ala Ser Leu Met
    210


<210> SEQ ID NO 36
<211> LENGTH: 801
<212> TYPE: DNA
<213> ORGANISM: Bacillus sp. strain ZI340
<220> FEATURE:
<221> NAME/KEY: CDS
<222> LOCATION: (154)..(801)

<400> SEQUENCE: 36

actcagcatg atgatgaggc tattgatgtt gatattattt atgattatga ttatatccca      60

gtcttatcag tagagatcga tcctgaagat gtcgaggtac tcagtcaaga agaaggcatt     120

gcctatattg aggaagactt tgaagtatcc att caa cag act gta cct tgg ggc     174
                                     Gln Gln Thr Val Pro Trp Gly
                                     1               5

att caa aga gta caa gct cct gca gtt att aat cgt ggc att aat ggc      222
Ile Gln Arg Val Gln Ala Pro Ala Val Ile Asn Arg Gly Ile Asn Gly
        10                  15                  20

agt ggg gta cga gta gcg gtg ctt gat tca ggc att tcc act cat agt      270
Ser Gly Val Arg Val Ala Val Leu Asp Ser Gly Ile Ser Thr His Ser
    25                  30                  35

gat tta agc att tcc ggt ggc gta agc ttt gtc cct ggt gaa cca act      318
Asp Leu Ser Ile Ser Gly Gly Val Ser Phe Val Pro Gly Glu Pro Thr
40                  45                  50                  55

att tct gat gga aat ggc cat ggt aca cat gta gcg gga acg att gct      366
Ile Ser Asp Gly Asn Gly His Gly Thr His Val Ala Gly Thr Ile Ala
                60                  65                  70

gca ctt aat aac agc att ggt gtg gta ggt gtt gca ccg aat gct caa      414
Ala Leu Asn Asn Ser Ile Gly Val Val Gly Val Ala Pro Asn Ala Gln
            75                  80                  85

att tat gga gta aaa gtt cta gga gca aac ggt cgc gga agt gtg agc      462
Ile Tyr Gly Val Lys Val Leu Gly Ala Asn Gly Arg Gly Ser Val Ser
        90                  95                  100

ggt att gct cag gga tta gag tgg gcc gct aca aac aat atg gat att      510
Gly Ile Ala Gln Gly Leu Glu Trp Ala Ala Thr Asn Asn Met Asp Ile
    105                 110                 115

gca aac tta agc cta gga agt gac gca cca agc tca act ctt gaa caa      558
Ala Asn Leu Ser Leu Gly Ser Asp Ala Pro Ser Ser Thr Leu Glu Gln
120                 125                 130                 135

gct gtt aac ttt gcc acg agc aga ggt gta ctt gtt gtt gca gct tca      606
Ala Val Asn Phe Ala Thr Ser Arg Gly Val Leu Val Val Ala Ala Ser
                140                 145                 150
```

-continued

```
gga aat aac ggg tct gga aac gtt ggc ttc cct gca cgt tac gca aat      654
Gly Asn Asn Gly Ser Gly Asn Val Gly Phe Pro Ala Arg Tyr Ala Asn
            155                 160                 165

gca atg gca gtt gga gca aca gat caa aac aat aga cgc gct aac ttt      702
Ala Met Ala Val Gly Ala Thr Asp Gln Asn Asn Arg Arg Ala Asn Phe
        170                 175                 180

tca caa tat gga gca ggt ctt gat att gta gct cct gga gta ggt gta      750
Ser Gln Tyr Gly Ala Gly Leu Asp Ile Val Ala Pro Gly Val Gly Val
    185                 190                 195

caa agt aca tat cca ggc aat cgt tat gta agt atg aat agt aca tct      798
Gln Ser Thr Tyr Pro Gly Asn Arg Tyr Val Ser Met Asn Ser Thr Ser
200                 205                 210                 215

aag                                                                  801
Lys


<210> SEQ ID NO 37
<211> LENGTH: 216
<212> TYPE: PRT
<213> ORGANISM: Bacillus sp. strain ZI340

<400> SEQUENCE: 37

Gln Gln Thr Val Pro Trp Gly Ile Gln Arg Val Gln Ala Pro Ala Val
1               5                   10                  15

Ile Asn Arg Gly Ile Asn Gly Ser Gly Val Arg Val Ala Val Leu Asp
            20                  25                  30

Ser Gly Ile Ser Thr His Ser Asp Leu Ser Ile Ser Gly Gly Val Ser
        35                  40                  45

Phe Val Pro Gly Glu Pro Thr Ile Ser Asp Gly Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Gln Ile Tyr Gly Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met Asp Ile Ala Asn Leu Ser Leu Gly Ser Asp Ala
        115                 120                 125

Pro Ser Ser Thr Leu Glu Gln Ala Val Asn Phe Ala Thr Ser Arg Gly
    130                 135                 140

Val Leu Val Val Ala Ala Ser Gly Asn Asn Gly Ser Gly Asn Val Gly
145                 150                 155                 160

Phe Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ala Gly Leu Asp Ile
            180                 185                 190

Val Ala Pro Gly Val Gly Val Gln Ser Thr Tyr Pro Gly Asn Arg Tyr
        195                 200                 205

Val Ser Met Asn Ser Thr Ser Lys
    210                 215
```